(12) United States Patent
Adachi et al.

(10) Patent No.: US 9,100,758 B2
(45) Date of Patent: Aug. 4, 2015

(54) SOUND PRESSURE ASSESSMENT SYSTEM, AND METHOD AND PROGRAM THEREOF

(71) Applicant: Panasonic Corporation, Osaka (JP)

(72) Inventors: Shinobu Adachi, Nara (JP); Yumiko Kato, Osaka (JP); Koji Morikawa, Kyoto (JP); Jun Ozawa, Nara (JP); Hiroshi Nittono, Hiroshima (JP)

(73) Assignee: Panasonic Corporation, Osaka (JP)

( * ) Notice: Subject to any disclaimer, the term of this patent is extended or adjusted under 35 U.S.C. 154(b) by 287 days.

(21) Appl. No.: 13/675,009

(22) Filed: Nov. 13, 2012

(65) Prior Publication Data

US 2013/0070929 A1    Mar. 21, 2013

Related U.S. Application Data

(63) Continuation of application No. PCT/JP2011/006016, filed on Oct. 27, 2011.

(30) Foreign Application Priority Data

Nov. 12, 2010   (JP) ................................. 2010-253441

(51) Int. Cl.
*H04R 29/00* (2006.01)
*A61B 5/00* (2006.01)
(Continued)

(52) U.S. Cl.
CPC .......... *H04R 29/001* (2013.01); *A61B 5/04845* (2013.01); *A61B 5/125* (2013.01); *A61B 5/6814* (2013.01)

(58) Field of Classification Search
None
See application file for complete search history.

(56) References Cited

U.S. PATENT DOCUMENTS 3,895,298 A * 7/1975 Schollmeier .................. 375/226
5,360,388 A * 11/1994 Spindel et al. .................. 600/25
(Continued)

FOREIGN PATENT DOCUMENTS

| JP | 2004-179965 A | 6/2004 |
| JP | 2010-521906 A | 6/2010 |
| WO | 2008/038650 A1 | 4/2008 |

OTHER PUBLICATIONS

Haenschel, Corinna et al. "Gamma and beta frequency oscillations in response to novel auditory stimuli: A comparison of human electroencephalogram (EEG) data with in vitro models." PNAS Jun. 20, 2000 vol. 97 No. 13. pp. 7645-7650.*
Graimann, Bernhard et al. "Toward a Direct Brain Interface Based on Human Subdural Recordings and Wavelet-Packet Analysis." IEEE Transactions on Biomedical Engineering, vol. 51 No. 6, Jun. 2004.*
Begleiter, H. et al. "Visual Evoked Potentials and Affective Ratings of Semantic Stimuli." Plenum Publishing Corp. 1979.*
(Continued)

*Primary Examiner* — Curtis Kuntz
*Assistant Examiner* — Qin Zhu
(74) *Attorney, Agent, or Firm* — Renner, Otto, Boisselle & Sklar, LLP

(57) ABSTRACT

A sound pressure assessment system determines sounds to be presented by referring to a database retaining data of sounds, each of which is a pure tone. The system presents the determined sound as a first sound, and in a predetermined time after presenting the first sound, presents as a second sound a sound at least having the same frequency and the same sound pressure level as those of the first sound to the user. The system extracts an amount of change from an N1 component in response to the first sound to that in response to the second sound. The N1 components are negative components of an user's event-related potential based on points of presenting the first and second sounds as respective starting points. The system determines whether the sound pressure level of the presented sound is excessive to the user, based on the amount of change.

20 Claims, 15 Drawing Sheets

(51) Int. Cl.
*A61B 5/12* (2006.01)
*A61B 5/0484* (2006.01)

(56) References Cited

U.S. PATENT DOCUMENTS

| | | | | |
|---|---|---|---|---|
| 5,825,894 | A * | 10/1998 | Shennib | 381/60 |
| 5,923,764 | A * | 7/1999 | Shennib | 381/60 |
| 2003/0007657 | A1* | 1/2003 | Ludvigsen | 381/312 |
| 2003/0073921 | A1* | 4/2003 | Sohmer et al. | 600/544 |
| 2005/0018858 | A1* | 1/2005 | John | 381/60 |
| 2005/0208156 | A1* | 9/2005 | Ploch et al. | 424/728 |
| 2007/0293785 | A1* | 12/2007 | Litvak | 600/559 |
| 2008/0037797 | A1* | 2/2008 | Goldstein et al. | 381/56 |
| 2009/0209835 | A1* | 8/2009 | Diab et al. | 600/323 |
| 2009/0247895 | A1* | 10/2009 | Morikawa et al. | 600/544 |
| 2009/0292221 | A1* | 11/2009 | Viirre et al. | 600/544 |
| 2009/0326405 | A1* | 12/2009 | Makinen | 600/544 |
| 2010/0076339 | A1 | 3/2010 | Marcoux | |
| 2010/0142725 | A1* | 6/2010 | Goldstein et al. | 381/92 |
| 2010/0156617 | A1* | 6/2010 | Nakada et al. | 340/439 |

OTHER PUBLICATIONS

Davis, Hallowell. "Slow Cortical Reponses Evoked by Acoustic Stimuli." From the Central Institute for the Deaf, St. Louis 1965.*
International Search Report for corresponding International Application No. PCT/JP2011/006016 mailed Dec. 13, 2011.
Kimitsuki et al., "Inner Ear Auditory Testing in Patients with Normal Hearing Showing Hyperacusis", Audiology Japan 52, 2009, pp. 152-156 and concise explanation.
Thornton et al., "The objective estimation of loudness discomfort level using auditory brainstem evoked responses", 1987.
"Jishoukanrendeni (ERP) Manyuaru-P300 Wo Chushinni-" or "Event-Related Potential (ERP) Manual-mainly Concerning P300-", edited by Kimtaka Kaga et al., Shinohara Shuppan Shinsha, 1995, p. 30 and partial English translation.
Suzuki et al., "Chosei Nokanhanno-Sonokisoto Rinsho—", or "Auditory Brain Stem Response—It's Basics and Clinical Applications", 1985, pp. 384-385 and concise explanation.

* cited by examiner

AMPLITUDE RATIO CONCERNING N1 COMPONENT
(SECOND SOUND /FIRST SOUND)

RESULTS OF SUBJECTIVE REPORT EXPERIMENT

|        | MEAN (dBSPL) | STANDARD DEVIATION |
|--------|--------------|--------------------|
| before | 91.2         | 2.2                |
| after  | 94.0         | 1.2                |

|  | A | B |
|---|---|---|
| P1-N1 AMPLITUDE RATIO (SECOND SOUND / FIRST SOUND) | SMALLER THAN PREDETERMINED THRESHOLD VALUE | EQUAL TO OR GREATER THAN PREDETERMINED THRESHOLD VALUE |
| RESULT OF ANNOYANCE DETERMINATION | ANNOYING | APPROPRIATE LOUDNESS |

FIG. 10

| AUDIO FILE | RIGHT OR LEFT | FREQUENCY (Hz) | SOUND PRESSURE LEVEL (dBSPL) |
|---|---|---|---|
| R0250Hz080dB.wav | R | 250 | 80 |
| R0250Hz085dB.wav | R | 250 | 85 |
| R0250Hz090dB.wav | R | 250 | 90 |
| R0250Hz095dB.wav | R | 250 | 95 |
| R0250Hz100dB.wav | R | 250 | 100 |
| R0250Hz105dB.wav | R | 250 | 105 |
| R0250Hz110dB.wav | R | 250 | 110 |
| L0250Hz080dB.wav | L | 250 | 80 |
| L0250Hz085dB.wav | L | 250 | 85 |
| L0250Hz090dB.wav | L | 250 | 90 |
| L0250Hz095dB.wav | L | 250 | 95 |
| L0250Hz100dB.wav | L | 250 | 100 |
| L0250Hz105dB.wav | L | 250 | 105 |
| L0250Hz110dB.wav | L | 250 | 110 |
| R0500Hz080dB.wav | R | 500 | 80 |
| R0500Hz085dB.wav | R | 500 | 85 |
| R0500Hz090dB.wav | R | 500 | 90 |
| R0500Hz095dB.wav | R | 500 | 95 |
| R0500Hz100dB.wav | R | 500 | 100 |
| R0500Hz105dB.wav | R | 500 | 105 |
| R0500Hz110dB.wav | R | 500 | 110 |
| L0500Hz080dB.wav | L | 500 | 80 |
| L0500Hz085dB.wav | L | 500 | 85 |
| L0500Hz090dB.wav | L | 500 | 90 |
| L0500Hz095dB.wav | L | 500 | 95 |
| L0500Hz100dB.wav | L | 500 | 100 |
| L0500Hz105dB.wav | L | 500 | 105 |
| L0500Hz110dB.wav | L | 500 | 110 |
| R1000Hz80dB.wav | R | 1000 | 80 |
| ... | ... | ... | ... |

71 → L0250Hz105dB.wav

FIG.11          ANNOYANCE
| RIGHT OR LEFT EAR | FREQUENCY | SOUND PRESSURE LEVEL dBSPL | | | | | | |
|---|---|---|---|---|---|---|---|---|
| | | 80 | 85 | 90 | 95 | 100 | 105 | 110 |
| RIGHT | 250 | 0 | 0 | 0 | 0 | 1 | 1 | 1 |
| RIGHT | 500 | 0 | 0 | 0 | 1 | 1 | 1 | 1 |
| RIGHT | 1000 | 0 | 0 | 0 | 1 | 1 | 1 | 1 |
| RIGHT | 2000 | 0 | 0 | 1 | 0 | 1 | 1 | 1 |
| RIGHT | 4000 | 0 | 0 | 1 | 1 | 1 | 1 | 1 |
| LEFT | 250 | 0 | 0 | 0 | 0 | 1 | 1 | 1 |
| LEFT | 500 | 0 | 0 | 0 | 1 | 1 | 1 | 1 |
| LEFT | 1000 | 0 | 0 | 0 | 1 | 1 | 1 | 1 |
| LEFT | 2000 | 0 | 0 | 1 | 0 | 1 | 1 | 1 |
| LEFT | 4000 | 0 | 0 | 0 | 1 | 1 | 1 | 1 |

*FIG.14*

| HTL VALUE (dBSPL) | UCL PREDICTION VALUE (dBSPL) |
|---|---|
| 50 | 100 |
| 55 | 102.5 |
| 60 | 105 |
| 65 | 107.5 |
| 70 | 110 |
| 75 | 112.5 |
| 80 | 115 |
| 85 | 117.5 |
| 90 | 120 |

SOUND PRESSURE ASSESSMENT SYSTEM, AND METHOD AND PROGRAM THEREOF

This is a continuation of International Application No. PCT/JP2011/006016, with an international filing date of Oct. 27, 2011, which claims priority of Japanese Patent Application No. 2010-253441 filed on Nov. 12, 2010, the contents of which are hereby incorporated by reference.

BACKGROUND

1. Technical Field

The present application relates to a technique of assessing whether a speech sound has been comfortably heard or not. More specifically, the present disclosure relates to a sound pressure assessment system and the like for assessing levels of annoyance with respect to a pure tone, for the "fitting" of a hearing aid or the like to provide a sound of appropriate loudness for each individual user by adjusting the amount of amplification of sounds with respect to each frequency.

2. Description of the Related Art

In recent years, people suffering from presbycusis are increasing in number due to the aging society. Even among the young, due to increased opportunities for listening to loud music for long hours as well as other influences, there is an increasing number of people suffering from hypacusia associated with acoustic traumas. Moreover, due to the downsizing and improved performance of hearing aids, users feel less of a psychological barrier against wearing hearing aids. Against this background, there is an increasing number of users who wear hearing aids on a daily basis in order to improve their conversational aural distinction abilities.

A hearing aid is a device for compensating for the deteriorated hearing of a user by increasing the amplitude of signals of specific frequencies, among various frequencies that compose sounds that are difficult for the user to hear. The amount of sound amplification which a user desires in a hearing aid varies depending on the level of deterioration in the hearing of the user. Therefore, before beginning use of a hearing aid, "fitting" is required for adjusting the amount of sound amplification in accordance with the hearing of each user.

Fitting is performed in such a manner that the output sound pressure (i.e. fluctuations in air pressure that are perceivable as a sound) of each frequency from a hearing aid is at an MCL (most comfortable level: a sound pressure level that is felt comfortable to a user). Thus, it is considered that appropriate fitting is yet to be attained under (1) an insufficient amount of amplification, or (2) an excessive amount of amplification. For example, under an insufficient amount of amplification, aural distinction of audios is not achieved, thus falling short of the purpose of wearing a hearing aid. Under an excessive amount of amplification, although distinction of audios may be possible, there is a problem in that the user may feel annoyance, which prevents them from using the hearing aid over a long time. Therefore, a fitting needs to be done in such a manner that neither (1) nor (2) occurs. In particular, (2) has the danger of hurting the user's ears due to the possibility of presenting an excessively high sound volume from the hearing aid.

In a first step of fitting, an audiogram is measured. An "audiogram" is an evaluation of a hearing threshold value defining a smallest sound pressure of a pure tone that allows it to be heard. For example, an "audiogram" is a diagram in which, for each of a number of sounds of different frequencies, the smallest sound pressure level (decibel value) that the user can aurally comprehend is plotted against frequency (e.g., 250 Hz, 500 Hz, 1000 Hz, 2000 Hz, 4000 Hz).

In a next step of fitting, based on a fitting theory, which is a mathematical function for estimating an amount of amplification for each frequency, an amount of amplification for each frequency is determined. There are several kinds of fitting theories, for example: the half-gain method, in which an insertion gain of each frequency is made half of the hearing threshold value of that frequency; Berger's method, which, in addition to the above, slightly augments the amplification from 1000 Hz to 4000 Hz by taking into consideration the frequency band and level of conversational voices; the POGO method, which, based on the half-gain method, reduces the gains at 250 Hz and 500 Hz (where there is not so much speech sound information but a lot of noise component is included) by 10 dB and 5 dB, respectively; and the NAL-R method, which performs amplification so that a frequency of long-term sound analysis of words will fall around a comfortable level. There are also fitting theories which utilize not only the hearing threshold value, but also the information of an MCL and an "uncomfortable level" (hereinafter "UCL"), i.e., a sound pressure level so loud that the user feels uncomfortable, to determine an amount of gain adjustment. In that case, before determining an amount of gain adjustment, the UCL and MCL need to be measured or estimated.

The UCL is to be measured for each frequency, similarly to an audiogram. Conventionally, the UCL is measured based on subjective reporting. Specifically, a continuous sound may be presented with an ascending method (i.e., the sound pressure level is gradually increased) by using an audiometer, for example, and a sound pressure level which is so annoying (i.e., loud) that it's unbearable may be reported, this sound pressure level being measured as the UCL (Takashi KIMITSUKI et al., "Inner ear auditory testing in patients with normal hearing showing hyperacusis", 2009).

Moreover, methods for measuring a UCL by using an electroencephalogram are under development. For example, Thornton, A. R. et al., "The objective estimation of loudness discomfort level using auditory brainstem evoked responses", 1987 discloses a technique of estimating a UCL from the relationship between a V-wave latency in a brain stem response called the ABR (auditory brainstem response) and the intensity of a stimulation. A sound pressure level which is obtained by adding a constant (e.g., 15 or 10) to a sound pressure level at which a decrease in the V-wave latency caused by an increasing sound pressure level becomes saturated is defined as the UCL.

On the other hand, generally speaking, an MCL (most comfortable level) is difficult to be measured through subjective reporting, and therefore is often approximated as a gradient which is a half of the hearing threshold value (half gain) or a median between the UCL and the hearing threshold value.

SUMMARY

The prior art technique needs further improvement in view of assessment of a user state concerning whether a speech sound has been comfortably heard or not.

One non-limiting and exemplary embodiment disclosed herein is directed to an annoyance assessment system which takes an objective measurement of a UCL in a short time and/or with a high accuracy.

A sound pressure assessment system according to an embodiment comprises: a biological signal measurement section configured to measure an electroencephalogram signal of a user; a sound database retaining data of a plurality of sounds, each sound being a pure tone; a presentation sound determination section configured to determine a sound to be presented by referring to the sound database; an output section configured to present the sound determined by the presentation sound determination section as a first sound to the user, and in a predetermined time after presenting the first sound, configured to present as a second sound a sound at least having a same frequency and a same sound pressure level as those of the first sound to the user; an amount-of-change extraction section configured to extract an amount of change from an N1 component in response to the first sound to an N1 component in response to the second sound, the N1 component in response to the first sound being a negative component of an event-related potential of the electroencephalogram signal based on a point of presenting the first sound as a starting point, the N1 component in response to the second sound being a negative component of an event-related potential of the electroencephalogram signal based on a point of presenting the second sound as a starting point; and an annoyance determination section configured to determine whether the sound pressure level of the presented sound is excessive to the user, based on the amount of change extracted by the amount-of-change extraction section.

According to the present disclosure, there is provided a way to assess a user state concerning whether a speech sound has been comfortably heard or not.

These general and specific aspects may be implemented using a system, a method, and a computer program, and any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF DRAWINGS

FIG. 10 is a diagram showing an example of a sound DB 71.

FIG. 11 is a diagram showing an exemplary accumulation of results of annoyance determination by using a technique according to Embodiment 1 of the present disclosure.

FIG. 14 is a diagram showing exemplary UCL prediction values.

DETAILED DESCRIPTION

Figure 1:
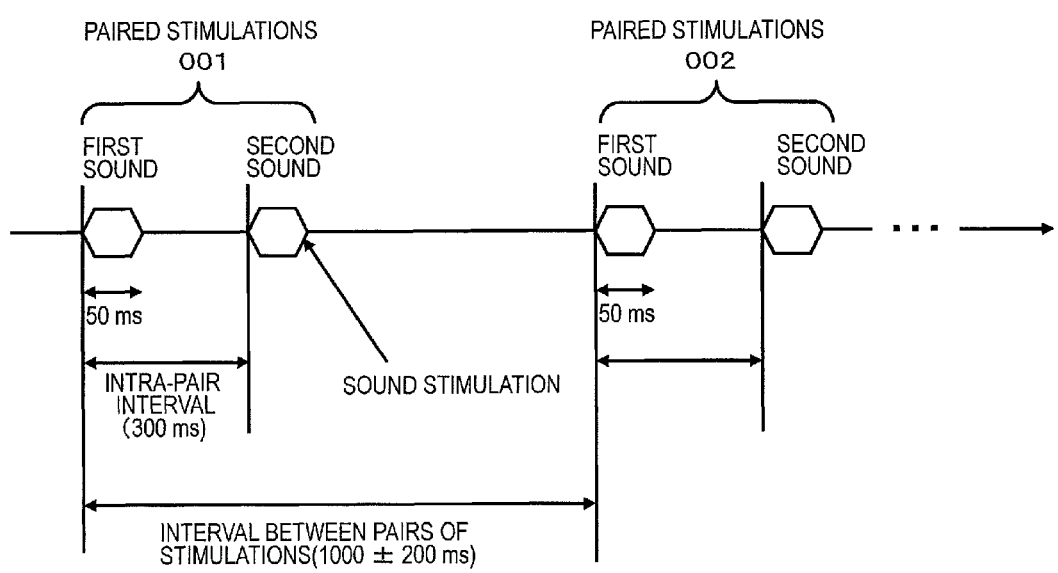
FIG. 1 shows a protocol of an electroencephalogram measurement experiment in outline.

The aforementioned UCL measurement through subjective reporting relies on ambiguous subjective reports as an index. Furthermore, the criterion as to a "sound pressure level so loud that it is felt uncomfortable" will vary from individual to individual and under the influence of linguistic expression, thus resulting in fluctuations. This has caused a problem of inability to precisely measure the UCL. Moreover, the need for the user to hear an overbearing continuous sound has led to the danger of hurting the user's ears.

On the other hand, a UCL estimation using an electroencephalogram relies on the ABR, which is a weak signal component, as an index. Therefore, it is necessary to repetitively present stimulations, on the order of 1000 times, for each of the sound pressure levels and frequencies to be subjected to UCL estimation, thus resulting in a problem of time consumingness. Long hours of testing would be a burden on the user.

Conventional techniques have had various problems as above. It is necessary to solve at least one, and preferably all, of such problems.

A sound pressure assessment system according to an embodiment includes: a biological signal measurement section configured to measure an electroencephalogram signal of a user; a sound database retaining data of a plurality of sounds, each sound being a pure tone; a presentation sound determination section configured to determine a sound to be presented by referring to the sound database; an output section configured to present the sound determined by the presentation sound determination section as a first sound to the user, and in a predetermined time after presenting the first sound, configured to present as a second sound a sound at least having a same frequency and a same sound pressure level as those of the first sound to the user; an amount-of-change extraction section configured to extract an amount of change from an N1 component in response to the first sound to an N1 component in response to the second sound, the N1 component in response to the first sound being a negative component of an event-related potential of the electroencephalogram signal based on a point of presenting the first sound as a starting point, the N1 component in response to the second sound being a negative component of an event-related potential of the electroencephalogram signal based on a point of presenting the second sound as a starting point; and an annoyance determination section configured to determine whether the sound pressure level of the presented sound is excessive to the user, based on the amount of change extracted by the amount-of-change extraction section.

As the amount of change, the amount-of-change extraction section may determine an amplitude ratio obtained by dividing an amplitude derived from the N1 component in response to the second sound by an amplitude derived from the N1 component in response to the first sound; and the annoyance determination section may compare the amount of change against a predetermined threshold value, and if the amount of change is smaller than the predetermined threshold value, determines that the sound pressure level of the presented sound is annoying to the user, and if the amount of change is equal to or greater than the predetermined threshold value, determines that the sound pressure level of the presented sound is an appropriate sound pressure level for the user.

The output section may present a plurality of pairs of stimulations, each pair including a said first sound and a said second sound; and for each pair of stimulations, the amount-of-change extraction section may extract an amount of change from an amplitude of a P1 component in response to the first sound, the P1 component being a positive component of an event-related potential of the electroencephalogram signal based on the point of presenting the first sound as a starting point, to an amplitude of a P1 component in response to the second sound, the P1 component being a positive component of an event-related potential of the electroencephalogram signal based on the point of presenting the second sound as a starting point, takes an arithmetic mean of event-related potentials of the extracted electroencephalogram signal for each of the first sounds and the second sounds of the plurality of pairs, and extracts as the amount of change a ratio of: a difference between an arithmetic-meaned amplitude value of the P1 component in response to the first sound and an arithmetic-meaned amplitude value of the N1 component in response to the first sound; and a difference between an arithmetic-meaned amplitude value of the P1 component in response to the second sound and an arithmetic-meaned amplitude value of the N1 component in response to the second sound.

As the amount of change, the amount-of-change extraction section may determine an absolute value of the difference between an amplitude derived from the N1 component in response to the second sound and an amplitude derived from the N1 component in response to the first sound; and the annoyance determination section may compare the amount of change against a predetermined threshold value, and if the amount of change is equal to or greater than the predetermined threshold value, determines that the sound pressure level of the presented sound is annoying to the user, and if the amount of change is smaller than the predetermined threshold value, determines that the sound pressure level of the presented sound is an appropriate sound pressure level for the user.

The N1 component may be a negative component of an event-related potential in a range from 80 ms to 130 ms after a point of presenting the first sound or the second sound from the output section.

The P1 component may be a positive component of an event-related potential in a range from 30 ms to 70 ms after a point of presenting the first sound or the second sound from the output section.

The sound database may retain each sound in association with at least one sound characteristic feature, the at least one sound characteristic feature including a right or left ear of the user to which the sound is presented, a frequency of the sound, and/or a sound pressure level of the sound; and the amount-of-change extraction section may take an arithmetic mean of event-related potentials of the electroencephalogram signal for each of the first sound and the second sound and each sound characteristic feature.

The amount-of-change extraction section may calculate a P1-N1 amplitude concerning an event-related potential in response to the first sound or the second sound, the P1-N1 amplitude being a difference between a positive peak value of an event-related potential from 30 ms to 70 ms after the point of presenting the first sound or the second sound as a starting point and a negative peak value from 80 ms to 150 ms after the point of presenting the first sound or the second sound as a starting point, and extracts as the amount of change an amplitude ratio between the P1-N1 amplitude in response to the second sound and the P1-N1 amplitude in response to the first sound; and if the amplitude ratio is smaller than a first threshold value, the annoyance determination section may determine that the sound pressure level of the presented sound is annoying to the user, and if the amplitude ratio is equal to or greater than the first threshold value, the annoyance determination section determines that the sound pressure level of the presented sound is an appropriate sound pressure level for the user.

The first threshold value may be 0.5.

The output section may present a plurality of pairs of stimulations, each pair including a said first sound and a said second sound; and for each pair of stimulations, the amount-of-change extraction section may extract a P2 component in response to the first sound, the P2 component being a positive component of the electroencephalogram signal from 160 ms to 250 ms after the point of presenting the first sound as a starting point, and a P2 component in response to the second sound, the P2 component being a positive component of the electroencephalogram signal from 160 ms to 250 ms after the point of presenting the second sound as a starting point, may take an arithmetic mean of event-related potentials of the extracted electroencephalogram signal for each of the first sounds and the second sounds of the plurality of pairs, and may extract as the amount of change a ratio of: a difference between an arithmetic-meaned amplitude value of the P2 component in response to the first sound and an arithmetic-meaned amplitude value of the N1 component in response to the first sound; to a difference between an arithmetic-meaned amplitude value of the P2 component in response to the second sound and an arithmetic-meaned amplitude value of the N1 component in response to the second sound.

The amount-of-change extraction section may calculate an N1-P2 amplitude concerning an event-related potential in response to the first sound or the second sound, the N1-P2 amplitude being a difference between a negative peak value from 80 ms to 150 ms after the point of presenting the first sound or the second sound as a starting point and a positive peak value of an event-related potential from 160 ms to 250 ms after the point of presenting the first sound or the second sound as a starting point, and extracts as the amount of change an amplitude ratio between the N1-P2 amplitude in response to the second sound and the N1-P2 amplitude in response to the first sound; and if the amplitude ratio is smaller than a second threshold value, the annoyance determination section may determine that the sound pressure level of the presented sound is annoying to the user, and if the amplitude ratio is equal to or greater than the second threshold value, the annoyance determination section may determine that the sound pressure level of the presented sound is an appropriate sound pressure level for the user.

The second threshold value may be 0.55.

The output section may present a plurality of pairs of stimulations, each pair including a said first sound and a said second sound, and presents a pair of stimulations of a different frequency from that of any immediately previously-presented pair of stimulations.

The sound pressure assessment system further include: a hearing threshold level input section configured to receive a hearing threshold value of the user; and an uncomfortable level prediction section configured to predict an uncomfortable level of the user based on the hearing threshold value having been input to the hearing threshold level input section. The presentation sound determination section may determine the first sound and second sound from within a predetermined range around the uncomfortable level predicted by the uncomfortable level prediction section.

A sound pressure assessment apparatus according to an embodiment includes: a presentation sound determination section configured to determine a sound to be presented by referring to a sound database retaining data of a plurality of sounds, each sound being a pure tone; an output section configured to present the sound determined by the presentation sound determination section as a first sound to the user, and in a predetermined time after presenting the first sound, configured to present as a second sound a sound at least having a same frequency and a same sound pressure level as those of the first sound to the user; an amount-of-change extraction section configured to extract an amount of change from an N1 component in response to the first sound to an N1 component in response to the second sound, the N1 component in response to the first sound being a negative component of an event-related potential of the electroencephalogram signal based on a point of presenting the first sound as a starting point, the N1 component in response to the second sound being a negative component of an event-related potential of the electroencephalogram signal based on a point of presenting the second sound as a starting point; and an annoyance determination section configured to determine annoyance with respect to the sound pressure level of the presented sound, based on the amount of change extracted by the amount-of-change extraction section.

A sound pressure assessment system according to an embodiment includes: a biological signal measurement section configured to measure an electroencephalogram signal of a user; a sound database retaining data of a plurality of sounds, each sound being a pure tone; a presentation sound determination section configured to determine a sound to be presented by referring to the sound database; an output section configured to present the sound determined by the presentation sound determination section as a first sound to the user, and in a predetermined time after presenting the first sound, configured to present as a second sound a sound at least having a same frequency and a same sound pressure level as those of the first sound to the user; an amount-of-change extraction section configured to extract an amount of change from an event-related potential in a zone from −100 milliseconds to 400 milliseconds based on a point of presenting the first sound as a starting point, to an event-related potential in a zone from −100 milliseconds to 400 milliseconds based on a point of presenting the second sound as a starting point; and an annoyance determination section configured to determine whether the sound pressure level of the presented sound is excessive to the user, based on the amount of change extracted by the amount-of-change extraction section.

A sound pressure assessment method according to an embodiment includes the steps of: measuring an electroencephalogram signal of a user; determining a sound to be presented to the user; presenting the determined sound to as a first sound to the user, and in a predetermined time after presenting the first sound, presenting as a second sound the same sound as the first sound to the user; extracting an amount of change from an N1 component in response to the first sound to an N1 component in response to the second sound, the N1 component in response to the first sound being a negative component of an event-related potential of the electroencephalogram signal based on a point of presenting the first sound as a starting point, the N1 component in response to the second sound being a negative component of an event-related potential of the electroencephalogram signal based on a point of presenting the second sound as a starting point; and determining annoyance with respect to the sound pressure level of the presented sound, based on the extracted amount of change.

The step of determining annoyance may compare the amount of change against a predetermined threshold value, and if the amount of change is smaller than the predetermined threshold value, may determine that the sound pressure level of the presented sound is annoying to the user, and if the amount of change is equal to or greater than the predetermined threshold value, may determine that the sound pressure level of the presented sound is an appropriate sound pressure level for the user.

A computer program stored on a non-transitory computer-readable medium, to be executed by a computer according to an embodiment, causes the computer to execute the steps of: receiving an electroencephalogram signal of a user; determining a sound to be presented to the user; presenting the determined sound to as a first sound to the user, and in a predetermined time after presenting the first sound, presenting as a second sound the same sound as the first sound to the user; extracting an amount of change from an N1 component in response to the first sound to an N1 component in response to the second sound, the N1 component in response to the first sound being a negative component of an event-related potential of the electroencephalogram signal based on a point of presenting the first sound as a starting point, the N1 component in response to the second sound being a negative component of an event-related potential of the electroencephalogram signal based on a point of presenting the second sound as a starting point; and determining annoyance with respect to the sound pressure level of the presented sound, based on the extracted amount of change.

The step of determining annoyance may compare the amount of change against a predetermined threshold value, and if the amount of change is smaller than the predetermined threshold value, may determine that the sound pressure level of the presented sound is annoying to the user, and if the amount of change is equal to or greater than the predetermined threshold value, may determine that the sound pressure level of the presented sound is an appropriate sound pressure level for the user.

According to the above, two pure tones of the same frequency and the same sound pressure level are successively presented; a characteristic feature(s) concerning an N1 component of the electroencephalogram is extracted respectively for the first sound and the second sound; and a UCL is estimated from an amount(s) of change in the characteristic feature(s). By utilizing amount(s) of change in the characteristic feature(s) in response to the first sound and the second sound, it is determined whether the sound pressure level of a presented sound is excessive to the user or not. Influences of individual differences can be avoided, and an annoyance assessment in a short time and with a high accuracy can be realized. As a result, the user will not feel annoyed when wearing a hearing aid, and a frequency gain setting can be realized such that fatigue is unlikely to occur even when the hearing aid is worn for long hours.

Hereinafter, with reference to the attached drawings, embodiments of the annoyance assessment system according to the present disclosure will be described.

An annoyance assessment system according to the present disclosure is employed for utilizing an electroencephalogram to assess, as a user state when listening to a pure tone, whether the user felt annoyed when listening to the pure tone. More specifically, the disclosed system successively presents two pure tones of the same frequency and the same sound pressure level, extracts a characteristic feature(s) concerning an N1 component of the electroencephalogram respectively for the first sound and the second sound, and assesses annoyance from an amount(s) of change in the characteristic feature(s).

First, the definitions of the terms used in the present specification will be described.

An "event-related potential (event-related potential: ERP)" is a kind of electroencephalogram (electroencephalogram: EEG), referring to a transient potential fluctuation in the brain which occurs in temporal relationship with an external or internal event.

An "N1 component" is a negative auditory evoked potential which is induced at about 100 ms since the presentation of an auditory stimulation as a starting point.

A "P1 component" is a positive auditory evoked potential which is induced at about 50 ms since the presentation of an auditory stimulation as a starting point.

A "P2 component" is a positive evoked potential which is induced at about 200 ms since the presentation of an auditory stimulation as a starting point.

A "negative component" refers to, generally speaking, a potential which is smaller than 0 µV.

A "positive component" refers to, generally speaking, a potential which is greater than 0 µV.

However, in the case where a comparison is made between two potentials, the potential that has the smaller value may be referred to as a negative component, and the potential that has the greater value may be referred to as a positive component. The comparison herein is based not only on their absolute values, but also takes plus/minus into consideration.

An "annoying sound pressure level" is a sound pressure level which is too loud for the user. For example, it refers to a sound pressure level so loud that the user feels uncomfortable.

An "appropriate sound pressure level" is a sound pressure level which is equal to or greater than a hearing threshold level (hereinafter "HTL") and which is not so annoying (i.e., loud) that the user feels uncomfortable.

"Presenting a sound" means outputting an auditory stimulation of a pure tone. For example, outputting a pure tone to only one ear from a pair of headphones falls within "presenting a sound".

A "pure tone" is a tone which repetitively undergoes periodic oscillation, such that it is expressed as a sine wave having only one frequency component.

In embodiments of the present disclosure, examples of using headphones to present a sound to a user will be illustrated. Although the headphones may be of any arbitrary type, they need to be able to precisely output a pure tone at a designated sound pressure level for enabling correct assessment.

In the present specification, in order to define a component of an event-related potential, a point in time after the lapse of a predetermined time since a given point is expressed by referring to a "latency of about 100 ms", for example. This means possible inclusion of a range around the specific point of 100 ms. Generally speaking, there are 30 to 50 ms of differences (shifts) in event-related potential waveform between individuals, according to table 1 on p. 30 of "JISHOUKANRENDENI (ERP) MANYUARU—P300 WO CHUSHINNI—(or "Event-Related Potential (ERP) Manual—mainly concerning P300-"), edited by Kimitaka KAGA et al., Shinohara Shuppan Shinsha, 1995)". Therefore, the terms "about X ms" and "near X ms" mean that a breadth of 30 to 50 ms may exist before or after X ms (e.g., 100 ms±30 ms, 200 ms±50 ms).

1. Experimental Outline

The inventors have conducted the following two experiments in order to identify an electroencephalogram characteristic component that reflects annoyance with respect to a pure tone, for the purpose of realizing an annoyance assessment for enabling objective measurements of a UCL in a short time and with a high accuracy.

A first experiment is an electroencephalogram measurement experiment where two pure tones of the same frequency and the same sound pressure level are successively presented with a predetermined interval therebetween, and event-related potentials in response to the first sound and the second sound are respectively measured. In the present specification, two stimulations which are successively presented in the aforementioned manner will be referred to as "paired stimulations". Note that the first sound and the second sound may not be of exactly the same frequency, but may be of frequencies with a difference which is not aurally distinguishable to humans. Note that the first sound and the second sound may not have exactly the same sound pressure level, but may have sound pressure levels with a difference which is not aurally distinguishable to humans.

A second experiment is a subjective report experiment where a UCL ("uncomfortable level", hereinafter this abbreviation will be used) is measured based on subjective reporting. One subjective report experiment each was conducted before and after the electroencephalogram measurement experiment. Then, by using the UCL obtained through the subjective report experiment as reference data, event-related potential components which are related to the UCL were looked for.

It was found as a result of this that, when paired stimulations of an overbearing sound pressure level exceeding what would be evaluated as an UCL through subjective reporting are presented, a characteristic feature(s) concerning the N1 component in response to the second sound is significantly reduced relative to the characteristic feature(s) concerning the N1 component in response to the first sound. From this finding, it was found that a UCL is estimatable by using as an index an amount(s) of change in the characteristic feature(s) concerning the respective N1 components for the first sound and the second sound. With this technique, a UCL can be assessed in a short time and with a high accuracy.

Hereinafter, these will be described in more detail. First, an electroencephalogram measurement experiment and a subjective report experiment which were conducted by the inventors in order to realize annoyance assessment will be described. Then, the construction and operation of embodiments of an annoyance assessment apparatus, and an annoyance assessment system including the annoyance assessment apparatus, will be described in outline.

2. Electroencephalogram Measurement Experiment and Subjective Report Experiment 2-1. Electroencephalogram Measurement Experiment In the electroencephalogram measurement experiment, paired stimulations were presented at a plurality of sound pressure levels, which were expected to include sound pressure levels which are greater than the sound pressure level corresponding to the UCL, and changes in characteristic features of the event-related potential in response to the first sound and the second sound were examined. Hereinafter, with reference to FIG. 1 to FIG. 4, experimental setting and experimental results of the electroencephalogram measurement experiment will be described.

The experimental participants were 12 adults, who were no longer in school, having normal hearing (28 to 49 years old).

The sound stimulations were toneburst sounds with a duration of 50 ms. Each sound had a rise and fall of 3 ms. In order to examine event-related potentials for different frequencies and different sound pressure levels, sound stimulations of five sound pressure levels (80, 85, 90, 95, 100 dBSPL) were prepared for each of three frequencies (1000, 2000, 4000 Hz). The sound stimulations were presented to one ear at a time through headphones. As paired stimulations, i.e., a first sound and a second sound, the same sound stimulation was successively presented twice to the same ear, with a predetermined interval therebetween.

FIG. 1 shows a protocol of the electroencephalogram measurement experiment in outline.

The participants were instructed that there was no need to pay attention to the sound stimulations. The interval between the first sound and second sound in one pair of stimulations (intra-pair interval) was fixed at 300 ms. On the other hand, the interval between the first sound of one pair of stimulations and the first sound of a next pair of stimulations (interval between pairs of stimulations) was randomly determined within a range of 1000±200 ms. Two blocks of experiments were conducted, where 750 pairs of stimulations constituted one block.

The sound stimulations to be presented as paired stimulations are preferably determined under the following constraints. Preferably, no sound stimulations of the same frequency as that of immediately previous paired stimulations are selected. For example, when selecting paired stimulations 002 in FIG. 1, any sound stimulations of the same frequency as that of the immediately previous paired stimulations 001 are preferably not selected. The ear to which the paired stimulations are presented is randomly chosen between the right or left ear. However, it is preferable that not more than four pairs of stimulations are presented successively to either the right or left ear. It is believed that these constraints alleviate the influence of habituation of auditory evoked potentials that is associated with successive presentation of the same paired stimulations.

Figure 2A:
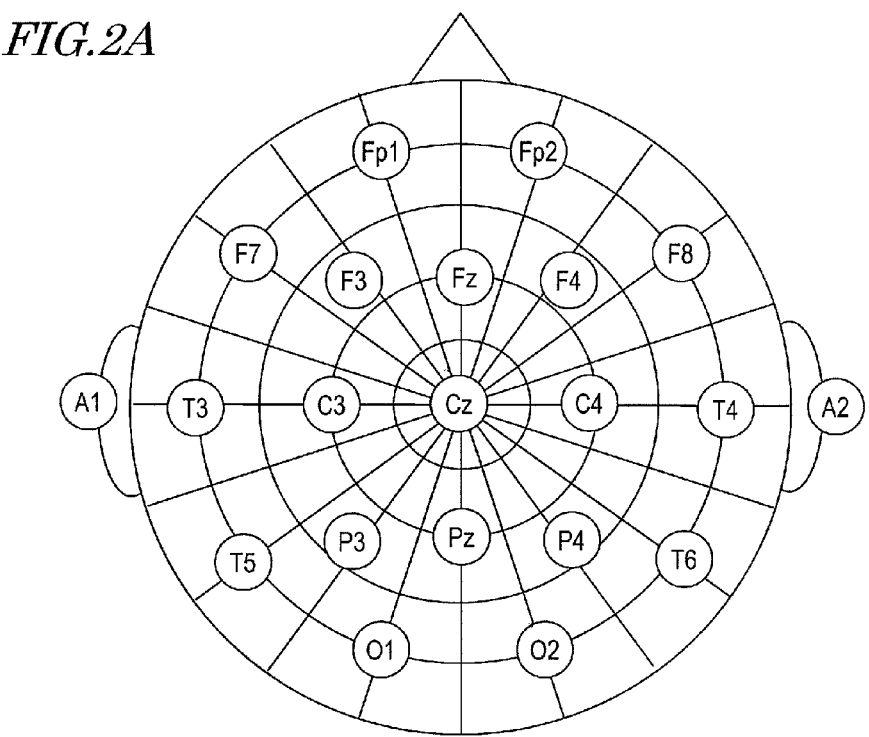
FIG. 2A is a diagram showing electrode positions according to the International 10-20 system.
Figure 2B:
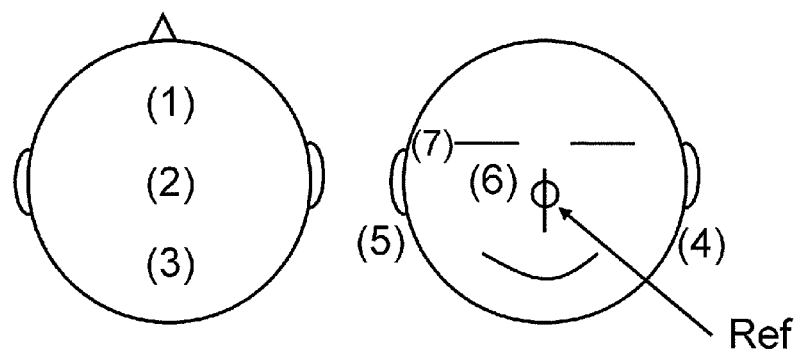
FIG. 2B is a diagram showing electrode positioning in the present experiment.

The electroencephalogram was recorded based on the nose, from Fz, Cz, Pz on the scalp (all according to the International 10-20 system), the right side of the right eye, under the right eye, or the right or left mastoid. A "mastoid" is a protrusion of the cranium below the hind root of an ear. FIG. 2A is a diagram showing the electrode positions according to the International 10-20 system (10-20 System). FIG. 2B shows electrode positioning in the present experiment.

The sampling frequency was 1000 Hz; the time constant was 1 second; and an analog low-pass filter was applied at 30 Hz. The electroencephalogram thus obtained was subjected to a 5 to 20 Hz digital band-pass filter off-line, and re-referenced on the basis of linked mastoids. As an event-related potential in response to each sound stimulation, a waveform from −100 ms to 400 ms was cut out based on the point in time of presenting the first sound or second sound as a starting point. As used herein, "−100 ms" means a point in time which is 100 milliseconds before the point in time at which a sound stimulation was presented.

In order to examine the overall tendency of electroencephalographic traits for each sound pressure level, the inventors have taken a total arithmetic mean of event-related potentials in response to the first sound and second sound with respect to each sound pressure level, irrespective of the frequency. Moreover, in order to examine the electroencephalographic traits of each individual person with respect to each of the right and left ears, each frequency, and each sound pressure level, the inventors took an arithmetic mean of event-related potentials of each individual person, in response to the first sound and second sound, with respect to each of the right and left ears, each frequency, and each sound pressure level. Those trials which exhibited an amplitude with an absolute value or 50 μV or more at any electrode were excluded from the total arithmetic mean or arithmetic mean.

Then, as characteristic features to serve as an index of annoyance assessment, two characteristic features concerning an N1 component which is induced at about 100 ms after sound stimulation presentation were ascertained.

A first characteristic feature is obtained by subtracting a zone average potential extending 10 ms before and after the negative peak of an N1 component, from a zone average potential extending 10 ms before and after the positive peak of a P1 component which is induced at about 50 ms after sound stimulation presentation. This characteristic feature will hereinafter be referred to as a "P1-N1 amplitude".

A second characteristic feature is obtained by subtracting a zone average potential extending 10 ms before and after the negative peak of an N1 component, from a zone average potential extending 25 ms before and after the positive peak of a P2 component which is induced at about 200 ms after sound stimulation presentation. This characteristic feature will hereinafter be referred to as an "N1-P2 amplitude".

Hereinafter, results of the electroencephalogram measurement experiment will be described.

Figure 3:
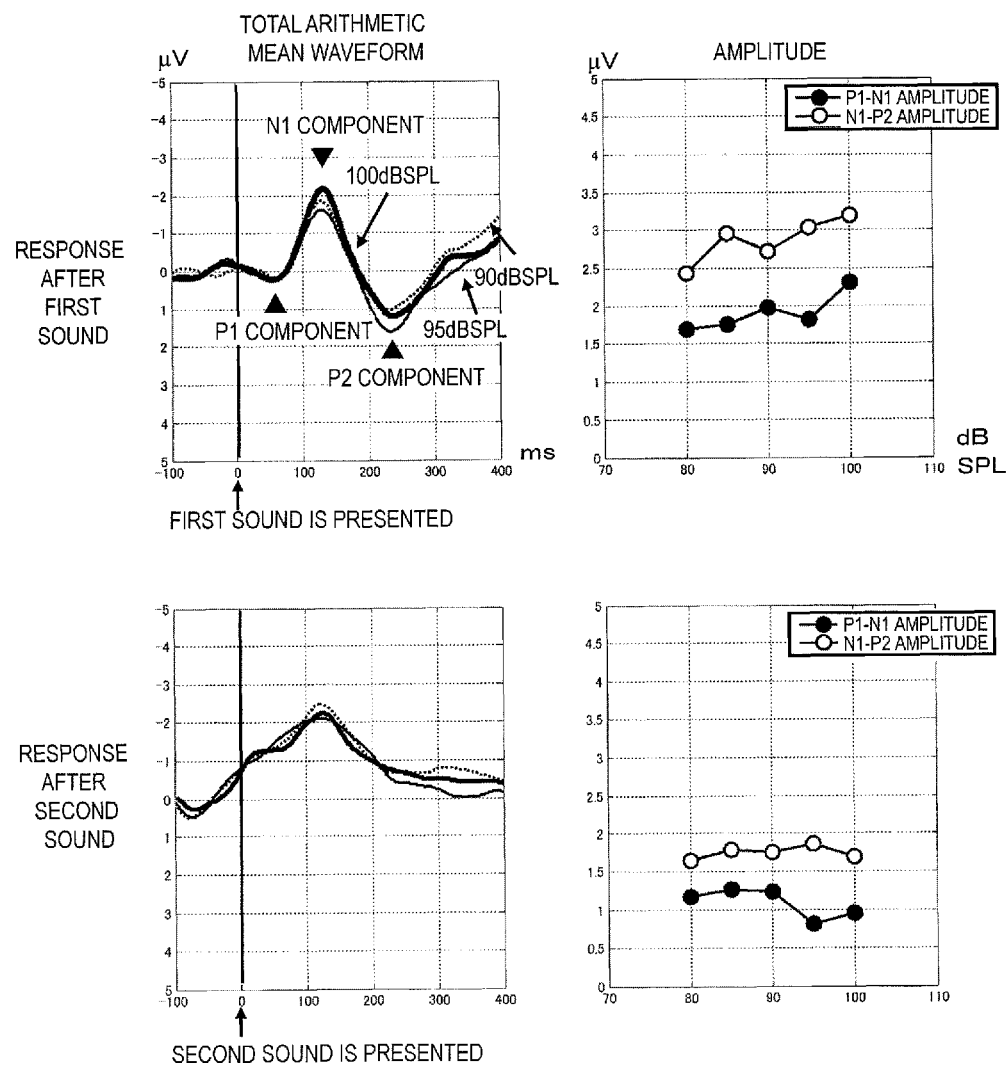
FIG. 3 is graphs showing waveforms of event-related potentials at a central portion (Cz), based on a point of presenting a first sound stimulation or a second sound stimulation as a starting point, where arithmetic means are taken for different sound pressure levels, and graphs in which P1-N1 amplitude and N1-P2 amplitude are plotted at different sound pressure levels.

The two graphs on the left-hand side of FIG. 3 show total arithmetic mean waveforms of event-related potentials at the central portion (Cz) in response to the first sound and the second sound, where total arithmetic means are taken for different sound pressure levels. The upper graph shows total arithmetic mean waveforms in response to the first sound, whereas the lower graph shows total arithmetic mean waveforms in response to the second sound. The horizontal axis represents time in units of ms, whereas the vertical axis represents potential in units of μV. On the horizontal axis, 0 ms marks a point in time at which the sound stimulation is presented.

As is clear from the scales shown in FIG. 3, the lower direction in the graphs corresponds to plus (positive), and the upper direction corresponds to minus (negative). In FIG. 3, waveforms of when presenting sound stimulations of 90, 95, and 100 dBSPL are indicated by a broken line, a thin solid line, and a bold solid line, respectively. It can be seen that, in response to the sound stimulation of any sound pressure level, an N1 component (negative peak) is induced at about 100 ms after sound stimulation presentation.

The two graphs on the right-hand side of FIG. 3 illustrate amplitude values of the aforementioned first and second characteristic features for each sound pressure level, as derived from the total arithmetic mean. The horizontal axis represents the sound pressure level in units of dBSPL, whereas the vertical axis represents the amplitude in units of μV. Black circles indicate P1-N1 amplitude, whereas white circles indicate N1-P2 amplitude. As shown in the upper right graph, both amplitude values in response to the first sound gently increase with an increase in the sound pressure level of the sound stimulation. On the other hand, it can be seen from the lower right graph that the P1-N1 amplitude in response to the second sound decreases at sound stimulations of sound pressure levels greater than 90 dBSPL, relative to the sound pressure levels smaller than 90 dBSPL.

Figures 4, 5:
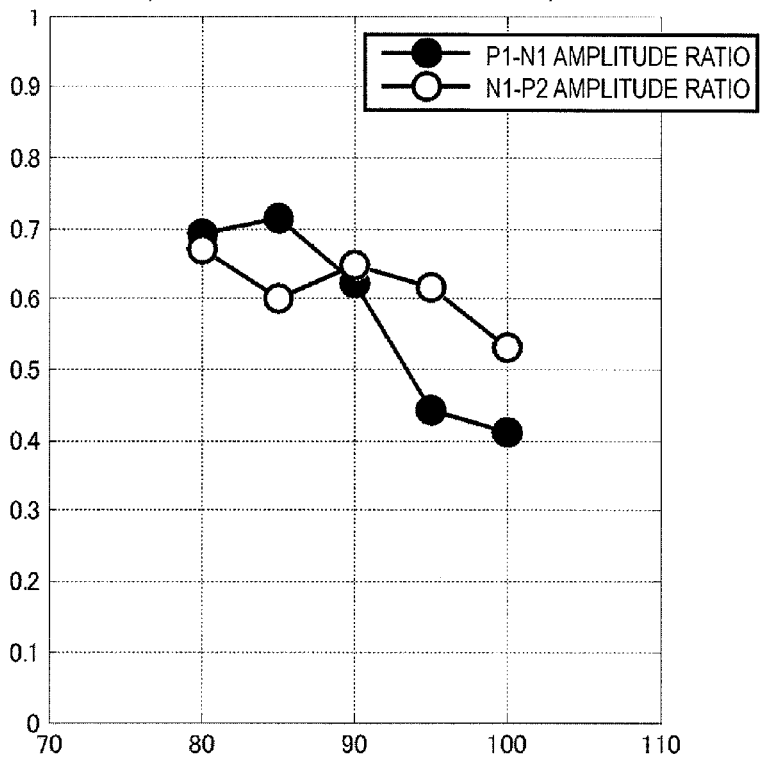
FIG. 4 is a graph in which P1-N1 amplitude ratios and N1-P2 amplitude ratios are plotted.
FIG. 5 is a diagram showing results of a subjective report experiment.

FIG. 4 shows amounts of change in the characteristic features concerning the N1 component. These amounts were obtained by dividing the amplitude in response to the second sound by the amplitude in response to the first sound, for each of the P1-N1 amplitude and N1-P2 amplitude. Black circles indicate the P1-N1 amplitude ratio, whereas the white circle indicate the N1-P2 amplitude ratio. The horizontal axis represents the sound pressure level value in units of dBSPL. By taking the P1-N1 amplitude ratio indicated by the black circles, for example, a P1-N1 amplitude ratio at 80 dBSPL is about 0.7. This value is obtained from a division (fraction) whose numerator is the value (about 1.2 µV) at 80 dBSPL in the lower right graph of FIG. 3 and whose denominator is the value (about 1.7 µV) at 80 dBSPL in the upper right graph of FIG. 3. Any other sound pressure level value on the horizontal axis of FIG. 4 is similarly obtained from a division (fraction) whose numerator is the potential in the lower right graph of FIG. 3 and whose denominator is the potential in the upper right graph of FIG. 3, as corresponding to each sound pressure level value. The values obtained through this calculation define the values on the vertical axis of FIG. 4. The N1-P2 amplitude ratio as indicated by the white circles in FIG. 4 is also similarly determined.

As shown in FIG. 4, both amplitude ratios decrease as the sound pressure level increases. Particularly in the P1-N1 component (black circles), it can be seen that the amplitude ratio in response to any sound stimulation of a sound pressure level greater than 90 dBSPL is significantly reduced relative to the amplitude ratio in response to a sound pressure level of 90 dBSPL or less.

2-2. Subjective Report Experiment

One subjective report experiment each was conducted before and after the electroencephalogram measurement experiment. As in KIMITSUKI et al., supra, a continuous sound was presented with an ascending method by using an audiometer, and a sound pressure level that was unbearably annoying was reported, this sound pressure level being defined as a UCL. For each of three frequencies (1000, 2000, 4000 Hz) to be presented in the electroencephalogram measurement experiment, measurements were taken for both ears, one ear at a time. In order to prevent anticipation of the sound pressure level, the sound pressure level at the start of the experiment was randomly selected from among 60, 65, and 70 dBHL. The sound pressure level of the continuous sound was increased in increments of 5 dB. An unbearably annoying sound pressure level was reported by raising a hand. Immediately after the participant raised a hand, the sound presentation was stopped, and the sound pressure level was recorded.

Hereinafter, results of the subjective report experiment will be described.

The results of the subjective report experiment greatly differed from individual to individual (by a maximum of 40 dB at the same frequency), although all participants were people with normal hearing. This indicates that the definition of "unbearably annoying" may greatly differ from individual to individual. Thus, it can be said that UCL evaluation through subjective reporting is difficult.

FIG. 5 shows mean values and variances (standard deviations) of the UCL evaluation results which were measured through subjective reporting. The unit of the sound pressure level was converted from dBHL to dBSPL, for matching with the electroencephalogram measurement experiment. Since the results of UCL measurement through subjective reporting fluctuate, in order to find an overall tendency, an arithmetic mean for the results of all participants was taken, irrespective of the frequency of the sound for presentation. The results of the subjective report experiment conducted before and after the electroencephalogram measurement experiment are indicated with the before- and after-labels. As compared to the results before the electroencephalogram measurement experiment (before), the UCL was significantly increased in the results after the electroencephalogram measurement experiment (after) (p<0.001); however, both were within the range of 90 to 95 dBSPL.

Note that the results of the subjective report experiment had fluctuations of 5 dB or more between before and after, in 58% among all results for each participant and each frequency. This indicates that annoyance assessment through subjective reporting is not free of ambiguity.

2-3. Discussions Based on Both Experiments

As shown in FIG. 5, among the results of the subjective report experiment, the sound pressure levels which were reported by the participants as unbearably annoying were in the range from 90 to 95 dBSPL. Moreover, among the results of the electroencephalogram measurement experiment shown in FIG. 4, the P1-N1 amplitude ratio was significantly reduced when the paired stimulations had a sound pressure level from 90 to 95 dBSPL. From these results, the inventors have found the correlation that the P1-N1 amplitude ratio significantly decreases near a sound pressure level which is a subjective UCL. Based on this correlation, it can be said that annoyance assessment concerning UCL can be realized by using as an index an amount of change in the characteristic feature concerning the N1 component between the first and second sounds in paired stimulations.

Specifically, an annoyance assessment can be realized with the following method. For example, the P1-N1 amplitude ratio may be compared against a predetermined threshold value (e.g. 0.5), and the smallest sound pressure level which has resulted in an amplitude ratio that is smaller than the threshold value may be assessed as a UCL. Incidentally, a P1-N1 amplitude ratio which was calculated from an arithmetic mean waveform with respect to each individual person, each of the right and left ears, each frequency, and each sound pressure level was compared against a predetermined threshold value to estimate respective UCLs, and these were further compared against the UCLs that were obtained in the subjective report experiment, which indicated an error of 5 dBSPL or less in 61.9%.

Although the above example illustrates a case where the P1-N1 amplitude ratio is utilized, an amplitude difference may be utilized instead of an amplitude ratio. Specifically, an amplitude in response to the first sound may be subtracted from an amplitude in response to the second sound to determine an amount of change in the characteristic feature concerning the N1 component. The correlation that the P1-N1 amplitude ratio significantly decreases near a sound pressure level which is a subjective UCL is also conserved when relying on results of subtraction. Accordingly, if an absolute value of the amplitude difference is equal to or greater than a certain threshold value, it may be determined that the user is being annoyed; and if the amplitude difference is smaller than the threshold value, it may be determined that the sound pressure level is appropriate for the user.

It is considered that the accuracy of UCL estimation can be enhanced by improving the method of extracting the characteristic features concerning the N1 component as well as the method of identification. For example, instead of an amplitude, wavelet coefficients that are obtained by applying a wavelet transformation to the event-related potential may be used as the characteristic feature, and an amount of change in a wavelet coefficient for a specific point in time and frequency may be utilized to make a determination.

Moreover, the determination itself may be made by employing a distinction algorithm such as linear discrimination or SVM (support vector machine), instead of making a comparison against a threshold value. In that case, no predetermined threshold value is required. When any such distinction algorithm is employed, characteristic amounts of event-related potentials in response to sound stimulations which are smaller, and those which are equal to or greater than, a sound pressure level that is a previously-acquired UCL of a generic user may be used as training data. For the purpose of confirming the ability to estimate a UCL by relying on a P1-N1 amplitude ratio as an index, the present experiment took total arithmetic means of the electroencephalograms and subjective report results of 12 participants; however, the aforementioned modifications of the method of characteristic amount extraction and the method of identification would allow an amount of change in a characteristic feature concerning the N1 component to be extracted even through an arithmetic mean of about 20 summations taken with respect to each user, each of the right and left ears, each frequency, and each sound pressure level.

It is known from conventional studies that the latency and N1-P2 amplitude of an N1 component in response to a pure-tone auditory stimulation (tone pip, toneburst) change in accordance with the intensity and rise time of the sound stimulation (see Suzuki et al., 1985, CHOSEI NOKANH-ANNO—SONOKISOTO RINSHO—, or "Auditory Brain Stem Response—Its Basics And Clinical Applications—, pp. 384-385). Specifically, within the range of sound pressure levels that are smaller than a predetermined sound pressure level, the latency of the N1 component decreases and the N1-P2 amplitude increase as the intensity of the stimulation sound increases. Moreover, at or above the predetermined sound pressure level, the decrease in the N1 component latency and the increase in the N1-P2 amplitude become saturated. As used herein, "saturation" means that the amounts of change regarding the decrease in the N1 component latency and the increase in the N1-P2 amplitude, which occur with an increase in the sound pressure level of the sound stimulation, become smaller than predetermined values.

As shown in the upper right graph of FIG. 3, the N1-P2 amplitude in response to the first sound generally increased with an increase in the sound pressure level, up to the sound pressure level near 90-95 dBSPL, which was reported to be the UCL in the subjective report experiment. Moreover, the increase in amplitude was saturated at any greater sound pressure level. Thus, it is considered that the UCL can be measured through a comparison of the N1-P2 amplitude in response to the first sound against a predetermined threshold value, or by detecting saturation of the increase in the N1-P2 amplitude with an increase in the sound pressure level.

However, the amplitude of an event-related potential has large individual differences, which makes it necessary to set a threshold value for each individual person; moreover, the increase in the N1-P2 amplitude is gentle. Therefore, a UCL estimation which relies on the N1-P2 amplitude in response to the first sound as the only index may possibly have a low accuracy. In fact, when the P1-N1 amplitude or the N1-P2 amplitude in response to the first sound in paired stimulations was used for determination against a predetermined threshold value, the resultant accuracy of estimation was significantly lower than the case where the P1-N1 amplitude ratio or N1-P2 amplitude ratio between the first sound and the second sound was used.

Therefore, it can be said that a high-accuracy annoyance assessment can be realized in a short time by presenting paired stimulations, and utilizing as an index an amount of change in the characteristic feature (P1-N1 amplitude) concerning the N1 component in response to the first sound and second sound, which significantly decreases near the sound pressure level which is the UCL. Since the amount of change in the characteristic feature between the first sound and second sound is a result of comparison in a characteristic component which is induced for each individual person, a robust annoyance assessment can be realized which is not susceptible to the influences of individual differences in the event-related potential.

It was found from the lower right graph of FIG. 3 that, also regarding the characteristic amounts concerning the amplitude of an N1 component in response to the second sound, the increase in amplitude with an increase in the sound pressure level becomes saturated near the sound pressure level which is evaluated to be the UCL through subjective reporting. In particular, the P1-N1 amplitude decreased at sound pressure levels equal to or greater than the sound pressure level which was evaluated to be the UCL through subjective reporting. Therefore, the UCL can also be measured through a comparison of the characteristic amount related to the amplitude of the N1 component in response to the second sound against a predetermined threshold value (e.g. 1.0 µV), or by detecting saturation of the increase in the characteristic amount related to the amplitude of the N1 component with an increase in the sound pressure level of the second sound.

Thus, it has become clear through the electroencephalogram measurement experiment and subjective report experiment conducted by the inventors that the characteristic features concerning an N1 component of the event-related potential based on the points of presenting the first sound and second sound in paired stimulations as starting points significantly change near the sound pressure level which is the UCL. This makes possible an annoyance assessment by relying on the P1-N1 amplitude ratio of event-related potentials in response to the paired stimulations as an index, for example.

Figures 6, 7:
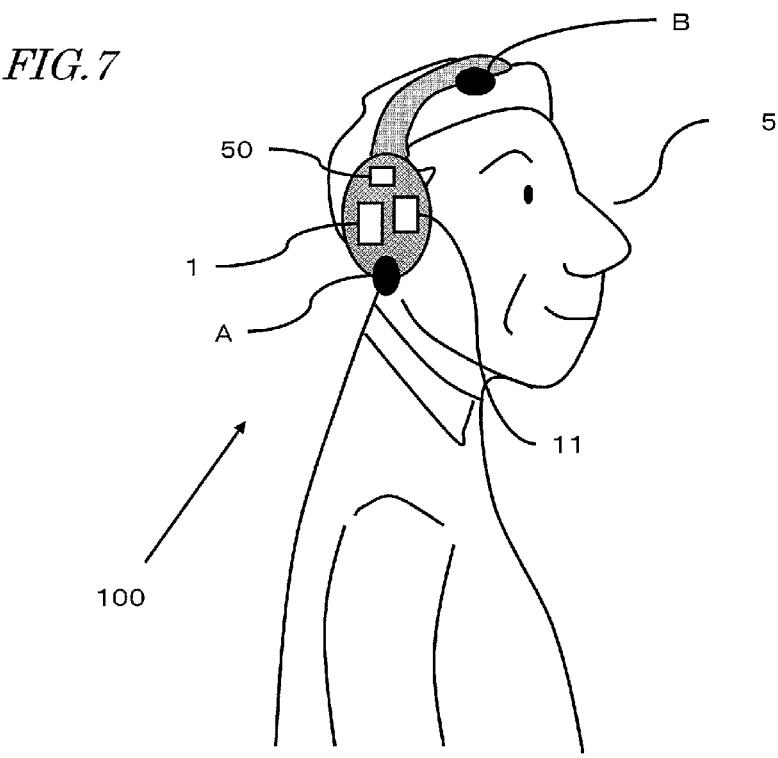
FIG. 6 is a diagram showing correspondence between the P1-N1 amplitude ratio and annoyance determination, as compiled by the inventors.
FIG. 7 is a diagram showing a construction and an environment of use for an annoyance assessment system 100 according to Embodiment 1 of the present disclosure.

FIG. 6 shows correspondence between the P1-N1 amplitude ratio and annoyance determination, as compiled by the inventors. If the P1-N1 amplitude ratio is smaller than the predetermined threshold value, an "annoying" determination is made; and if it is equal to or greater than the predetermined threshold value, an "appropriate loudness" determination is made.

Hereinafter, annoyance assessment systems according to embodiments of the present disclosure will be described. An annoyance assessment system presents paired stimulations, and realizes an annoyance assessment based on an amount(s) of change in the characteristic feature(s) concerning the N1 component in event-related potentials in response to the first sound and second sound in paired stimulations. This is unprecedentedly realized based on the aforementioned findings of the inventors. The following embodiments illustrate examples where an amplitude ratio obtained by dividing an amplitude in response to the second sound by an amplitude in response to the first sound is utilized. However, as mentioned above, an amplitude difference may be utilized instead of an amplitude ratio, for example. In this case, the component element(s) for calculating the amplitude ratio may calculate an absolute value of the amplitude difference, and a threshold value adapted to the amplitude ratio may be replaced by a threshold value adapted to an absolute value of the amplitude difference.

Embodiment 1

Hereinafter, an annoyance assessment system will be described in outline first. Thereafter, the construction and operation of an annoyance assessment system including the annoyance assessment apparatus will be described.

An annoyance assessment system according to the present embodiment presents paired stimulations, extracts a characteristic feature concerning an N1 component of the electroencephalogram respectively for the first sound and the second sound, and determines a UCL from an amount of change in the characteristic feature.

In the present embodiment, a probe electrode is placed at the central portion (Cz) and a reference electrode is placed at the right or left mastoid, and an electroencephalogram is measured as a potential difference between the probe electrode and the reference electrode. Note that the level and polarity of a characteristic component of an event-related potential may vary depending on the positions at which the electrodes for electroencephalogram measurement are worn, and the manner in which the reference electrode and the probe electrode are set. However, based on the following description, those skilled in the art should be able to make appropriate modifications depending on the specific reference electrode and probe electrode, and extract a characteristic feature of an event-related potential and make an annoyance assessment. Any such variant is encompassed within the present disclosure.

FIG. 7 shows a construction and an environment of use for the annoyance assessment system 100 of the present embodiment. The annoyance assessment system 100 is exemplified so as to correspond to a system construction of Embodiment 1 described later.

The annoyance assessment system 100 includes an annoyance assessment apparatus 1, a sound stimulation output section 11, and a biological signal measurement section 50. The biological signal measurement section 50 is connected to at least two electrodes A and B. Electrode A is attached at a mastoid of the user 5, whereas electrode B is attached at the central portion (so-called Cz) of the scalp of the user 5.

The annoyance assessment system 100 presents paired stimulations of a certain frequency and a certain sound pressure level to either the right or left ear of the user 5, and extracts a characteristic feature concerning an N1 component at a latency of about 100 ms, in electroencephalograms (event-related potentials) from the user 5 which are measured based on the points of presenting the first sound and the second sound as starting points. Then, it is determined whether the amount of change in the characteristic feature between the first sound and second sound is smaller than a predetermined threshold value, thus determining whether the user feels annoyed or not.

An electroencephalogram from the user 5 is acquired by the biological signal measurement section 50 based on a potential difference between electrode A and electrode B. The biological signal measurement section 50 sends information corresponding to the potential difference (electroencephalogram signal) to the annoyance assessment apparatus 1. Although FIG. 7 illustrates an example where the annoyance assessment apparatus 1 is within the same housing as the biological signal measurement section 50 and the sound stimulation output section 11, the annoyance assessment apparatus 1 may be in a separate housing. In that case, the electroencephalogram signal measured by the biological signal measurement section 50 is sent to the annoyance assessment apparatus 1 in a wireless or wired manner.

The annoyance assessment apparatus 1 controls presentation timing of the sound stimulations for annoyance assessment, and presents sound stimulations to the user 5 via the sound stimulation output section 11 (e.g., loudspeaker of headphones).

Figure 8:
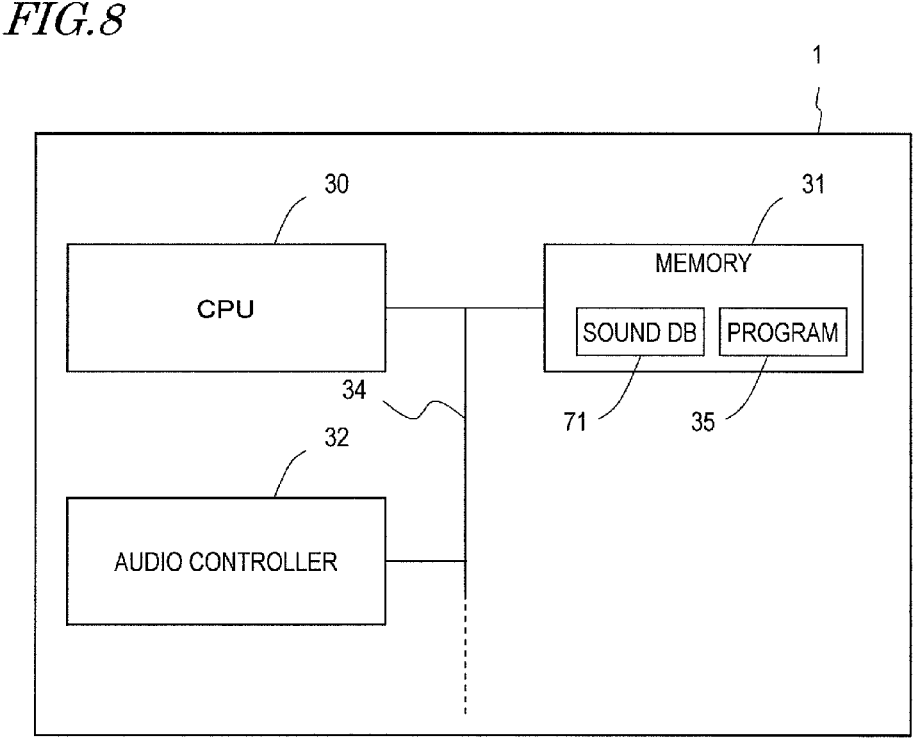
FIG. 8 is a diagram showing the hardware construction of an annoyance assessment apparatus 1 according to Embodiment 1 of the present disclosure.

FIG. 8 shows a hardware construction of the annoyance assessment apparatus 1 of the present embodiment. The annoyance assessment apparatus 1 includes a CPU 30, a memory 31, and an audio controller 32. These elements are interconnected via a bus 34 so that data exchange among them is possible.

The CPU 30 executes a computer program 35 which is stored in the memory 31. A processing procedure as illustrated by a subsequently-described flowchart is described in the computer program 35. In accordance with the computer program 35, the annoyance assessment apparatus 1 performs a process of controlling the entire annoyance assessment system 100, by utilizing a sound database (DB) 71 which is also stored in the same memory 31. This process will be described in detail later.

In accordance with instructions from the CPU 30, the audio controller 32 outputs the sound stimulations for presentation via the sound stimulation output section 11 at a designated sound pressure level.

Note that the annoyance assessment apparatus 1 may be implemented as a piece of hardware (e.g., a DSP) consisting of a semiconductor circuit having a computer program incorporated therein. Such a DSP can realize all functions of the aforementioned CPU 30, memory 31, and audio controller 32 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 8 (e.g., a PC) is able to function as the annoyance assessment apparatus 1 according to the present embodiment. Note that the sound DB 71 does not need to be stored in the memory 31, but may be stored on a hard disk (not shown) which is connected to the bus 34, for example.

Figure 9:
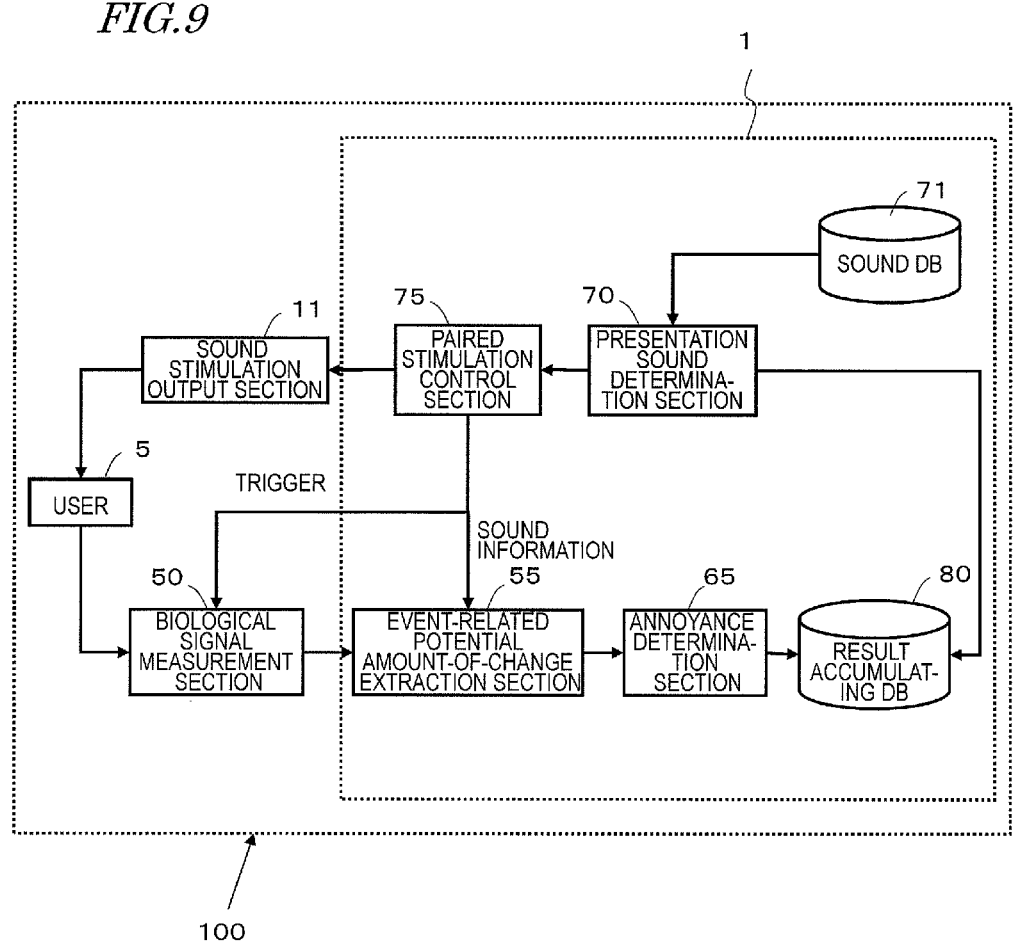
FIG. 9 is a diagram showing a functional block construction of the annoyance assessment system 100 according to Embodiment 1 of the present disclosure.

FIG. 9 shows a functional block construction of the annoyance assessment system 100 of the present embodiment. The annoyance assessment system 100 includes the sound stimulation output section 11, the biological signal measurement section 50, and the annoyance assessment apparatus 1. FIG. 9 also shows detailed functional blocks of the annoyance assessment apparatus 1. Specifically, the annoyance assessment apparatus 1 includes an event-related potential amount-of-change extraction section 55 (hereinafter referred to as an "amount-of-change extraction section 55"), an annoyance determination section 65, a presentation sound determination section 70, a sound DB 71, a paired stimulation control section 75, and a result accumulating DB 80. The user 5 block is illustrated for ease of explanation. The annoyance assessment apparatus 1 is connected wiredly or wirelessly to the sound stimulation output section 11 and the biological signal measurement section 50. Note that at least the presentation sound determination section 70, the sound stimulation output section 11, the amount-of-change extraction section 55, and the annoyance determination section 65 may be included in the annoyance assessment apparatus 1.

The respective functional blocks (except the sound DB 71) of the annoyance assessment apparatus 1 correspond to functions which are realized by the CPU 30, the memory 31, and the audio controller 32 as a whole upon executing the program which has been described in conjunction with FIG. 8.

The sound DB 71 is a database of sound stimulations which is provided for performing a annoyance assessment. FIG. 10 shows an exemplary sound DB 71 in the case where pure tones of a sound pressure level from 80 dBSPL to 110 dBSPL is used at a frequency from 250 Hz to 4000 Hz for each of the right and left ears, for example, in order to perform an annoyance assessment for each of the right and left ears and each frequency. The sound DB 71 shown in FIG. 10 retains sound stimulation files to be presented, as well as information of the right or left ear to present the sound stimulations to, and the frequencies and sound pressure levels of the sound stimulations. Each sound stimulation may be a toneburst sound (rise-fall 3 ms) with a duration of 50 ms, for example. The duration of the sound stimulation may be any value in a range where an N1 component is clearly induced, e.g., 25 ms or 100 ms.

FIG. 9 is again referred to. The presentation sound determination section 70 determines the right or left ear, frequency, and sound pressure level of the sound stimulation to be presented, by referring to the sound DB 71. The sounds for presentation may be randomly determined under the following constraints, for example: any sound stimulation that is of the same frequency as the immediately previous paired stimulations is preferably not selected; presentation is made to the right or left ear in random order; however, it is preferable that not more than four pairs of stimulations are presented successively to either the right or left ear. In this manner, the influence of habituation of electroencephalograms that is associated with successive presentation of the same paired stimulations is alleviated, whereby a highly accurate annoyance assessment can be realized. Then, the presentation sound determination section 70 sends the information of the determined sound stimulation to the paired stimulation control section 75.

Upon receiving the information of the sound stimulation from the presentation sound determination section 70, the paired stimulation control section 75 presents the sound stimulation in successive instances (i.e., first sound, second sound) at a predetermined intra-pair interval. The intra-pair interval is set to 100 ms or more, for example, in order to allow an N1 component in response to the first sound and an N1 component in response to the second sound to be clearly induced. Specifically, it may be 300 ms or 200 ms, for example. Moreover, the intra-pair interval may be arbitrarily set so long as the influence of the first sound is not lost, e.g., 10 seconds or less. The intra-pair interval may be retained in the paired stimulation control section 75, for example. In accordance with the points of presenting the sound stimulations of the first sound and second sound, the paired stimulation control section 75 outputs triggers to the biological signal measurement section 50. Moreover, the paired stimulation control section 75 sends the information concerning the right or left ear, frequency, sound pressure level, and intra-pair interval of the presented sound stimulations to the amount-of-change extraction section 55.

The sound stimulation output section 11 reproduces the sound stimulation determined by the presentation sound determination section 70 with its timing being controlled by the paired stimulation control section 75, and presents it to the user 5.

The biological signal measurement section 50, which is an electroencephalograph for measuring a biological signal of the user 5, measures an electroencephalogram as the biological signal. Then, the biological signal measurement section 50 subjects the electroencephalogram data to a frequency filtering with a cutoff frequency which is suitable for N1 component extraction, and cuts out an event-related potential in response to each of the first sound and second sound in a predetermined zone (e.g. a zone from −100 ms to 400 ms) based on a trigger received from the paired stimulation control section 75 as a starting point, and sends the waveform data (event-related potentials) to the amount-of-change extraction section 55. Since the N1 component frequency is about 10 Hz, in the case where a band-pass filter is used as the frequency filter, it may be set so as to allow e.g. 5 Hz to 15 Hz to pass through. It is assumed that the user 5 has already put on the electroencephalograph. The probe electrode for electroencephalogram measurement is attached at the central portion Cz, for example.

In accordance with the actual sound stimulation to be presented that is received from the paired stimulation control section 100, the amount-of-change extraction section 55 performs an arithmetic mean calculation for the event-related potentials received from the biological signal measurement section 50 in response to the first sound and second sound. The arithmetic mean calculation is performed by, for example, selecting only those event-related potentials which are in response to sound stimulations sharing the same characteristics (frequency and sound pressure level), for each of the first sound and second sound. Then, the amount-of-change extraction section 55 determines a characteristic feature concerning the N1 component for each of the first sound and the second sound, and calculates an amount of change in the characteristic feature. For example, in the case where a P1-N1 amplitude is to be utilized as a characteristic feature concerning the N1 component, for example, a value which is obtained by subtracting the minimum value at a latency of about 100 ms from the maximum value at a latency of about 50 ms may be adopted as the P1-N1 amplitude. Alternatively, a value which is obtained by subtracting a zone average potential within ±10 ms of a negative peak at a latency of about 100 ms from a zone average potential within ±10 ms of a positive peak at a latency of about 50 ms may be adopted as the P1-N1 amplitude, for example. Then, as an amount of change in the characteristic feature, an amplitude ratio which is obtained by dividing the amplitude in response to the second sound by the amplitude in response to the first sound is calculated, for example. The amount-of-change extraction section 55 sends the calculated amount of change in the characteristic feature concerning the N1 component to the annoyance determination section 65.

The annoyance determination section 65 receives the data of the amount of change in the characteristic feature concerning the N1 component from the amount-of-change extraction section 55, and performs an annoyance determination based on the amount of change. For example, if a P1-N1 amplitude ratio between the first sound and the second sound (amplitude in response to the second sound/amplitude in response to the first sound) is received from the amount-of-change extraction section 55, an annoyance determination is made based on this amplitude ratio. The determination may be performed through comparison against a predetermined threshold value, for example. In that case, if the amplitude ratio is smaller than the predetermined threshold value, an "annoying" determination is made; if the amplitude ratio is equal to or greater than the predetermined threshold value, an "appropriate loudness" determination is made. The predetermined threshold value may be 0.5, for example.

Note that the above-described functions of the amount-of-change extraction section 55 and the annoyance determination section 65 are only exemplary. Although a case is illustrated where the amount-of-change extraction section 55 detects an amount of change in the characteristic feature concerning the N1 component, it may be the annoyance determination section 65 that detects an amount of change.

Although the above description illustrates that the annoyance determination section 65 makes an "annoying" or "appropriate loudness" determination, the annoyance determination section 65 may merely determine a specific value.

For example, the P1-N1 amplitude ratio between the first sound and the second sound may be adopted as the determination result.

From the presentation sound determination section 70, the result accumulating DB 80 receives information concerning the right or left ear, frequency, and sound pressure level of the presented sound stimulation. Moreover, from the annoyance determination section 65, the result accumulating DB 80 receives information of a result of annoyance determination for each pair of stimulations. Then, information of the received annoyance determination result is accumulated with respect to each of the right or left ear, frequency, and sound pressure level of each sound stimulation, for example.

FIG. 11 shows an exemplary data accumulation in the result accumulating DB 80. FIG. 11 illustrates an example where annoyance information is accumulated with respect to each of the right and left ears, each frequency, and each sound pressure level. For example, in FIG. 11, "1" indicates that the annoyance determination section 65 has made an "annoying" determination, and "0" indicates that the annoyance determination section 65 has made an "appropriate loudness" determination. The reason why data is provided for each of the right and left ears is that the user may wear a hearing aid(s) on either one or both of the right and left ears. The right or left ear data is provided because the annoyance assessment system 100 of the present embodiment needs to make annoyance assessments with respect to either the right or left ear.

Figure 12:
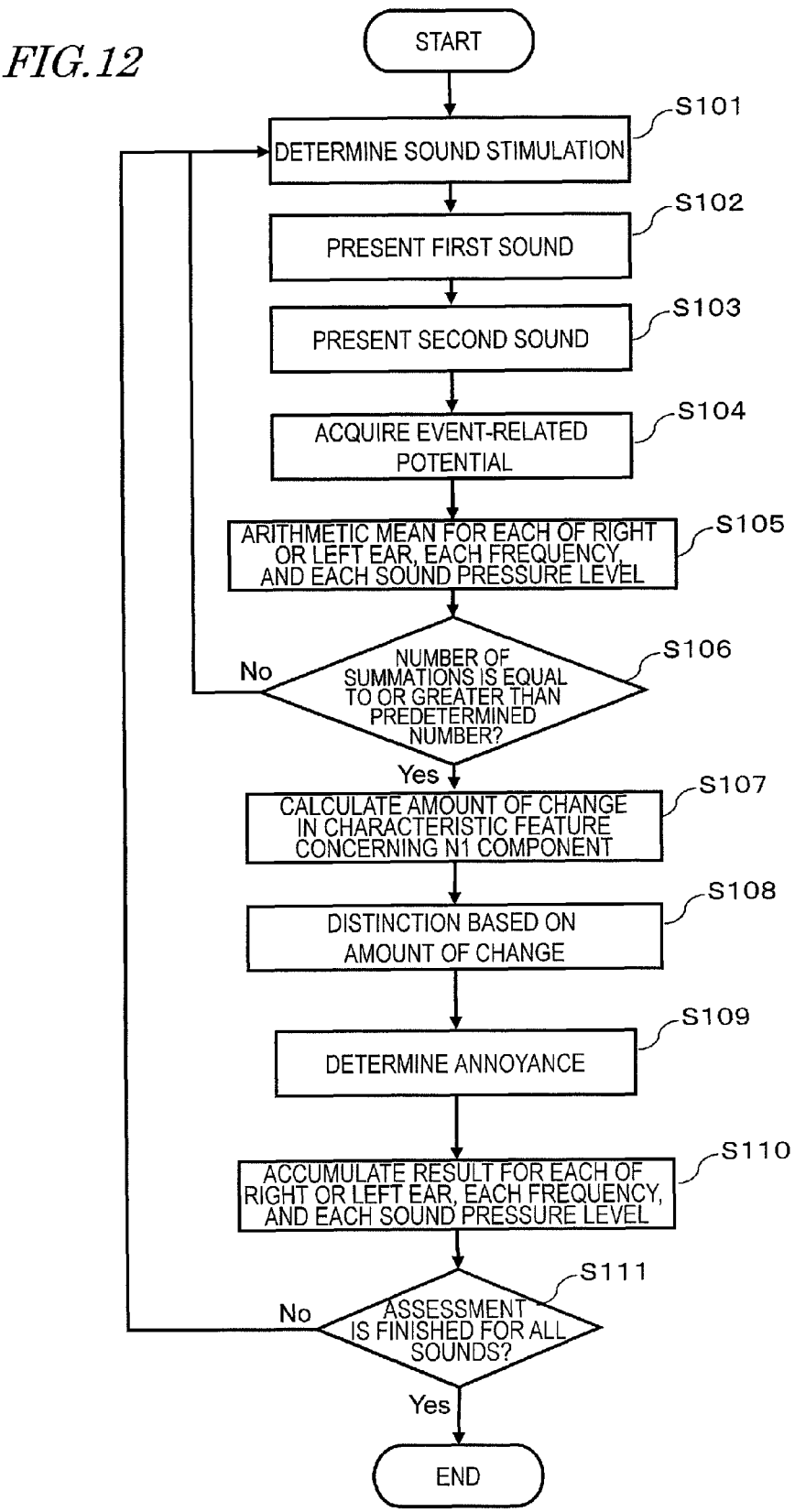
FIG. 12 is a flowchart showing a procedure of processing presented by the annoyance assessment system 100.

Next, with reference to FIG. 12, a processing procedure which is performed by the annoyance assessment system 100 of FIG. 9 will be described. FIG. 12 is a flowchart showing a procedure of processing by the annoyance assessment system 100.

Now, the electroencephalogram to be utilized by the annoyance assessment system 100 will be described. A negative electroencephalogram component which appears in a range from 80 ms to 150 ms after a sound stimulation is presented is measured as an N1 component. A positive electroencephalogram component which appears in a range from 30 ms to 70 ms after a sound stimulation is presented is measured as a P1 component. A positive electroencephalogram component which appears in a range from 160 ms to 250 ms after a sound stimulation is presented is measured as a P2 component.

At step S101, by referring to the sound DB 71, the presentation sound determination section 70 determines the right or left ear, frequency, and sound pressure level of the sound stimulation to be presented. Then, the information of the determined sound stimulation is sent to the paired stimulation control section 75. The sound stimulation may be randomly determined under the following constraints, for example. Any sound stimulation that is of the same frequency as the immediately previous paired stimulations is preferably not selected; the ear to which the paired stimulations are presented is randomly chosen between the right or left ear; however, it is preferable that not more than four pairs of stimulations are presented successively to either the right or left ear.

At step S102, the paired stimulation control section 75 presents the sound stimulation determined by the presentation sound determination section 70 to the user 5 via the sound stimulation output section 11 (first sound). Then, it sends a trigger to the biological signal measurement section 50, and sends information of the right or left ear, frequency, and sound pressure level of the presented sound stimulation to the amount-of-change extraction section 55.

At step S103, after a predetermined intra-pair interval from step S102, the paired stimulation control section 75 presents the sound stimulation determined by the presentation sound determination section 70 again to the user 5 via the sound stimulation output section 11 (second sound). The predetermined intra-pair interval may be retained in the paired stimulation control section 75, for example. Then, similarly to step S102, it sends a trigger to the biological signal measurement section 50, and sends information of the right or left ear, frequency, and sound pressure level of the presented sound stimulation to the amount-of-change extraction section 55. At step S102 and step S103, information of the intra-pair interval may further be sent to the amount-of-change extraction section 55.

At step S104, upon receiving a trigger from the paired stimulation control section 75, the biological signal measurement section 50 cuts out an event-related potential from e.g. −100 ms to 400 ms from the measured electroencephalogram, based on the trigger for the first sound or the second sound as a starting point. Then, an average potential from e.g. −100 ms to 0 ms is obtained, and the baseline of the resultant event-related potential is corrected so that an average potential thereof equals 0 μV. It is assumed that, during the assessment, the biological signal measurement section 50 is always measuring the electroencephalogram, and applying a frequency filter which is suitable for extracting the characteristic feature concerning the N1 component to the electroencephalogram data. A "suitable" frequency filter may be a band-pass filter which allows 5 Hz to 15 Hz to pass through, for example, between which 10 Hz (i.e., the center frequency of the N1 component) is interposed. In the case where a high-pass filter of e.g. 5 Hz or more is applied to the electroencephalogram data, the electroencephalogram data is hardly affected by changes in the baseline, so that the baseline correction is not required.

At step S105, based on information of the right or left ear, frequency, and sound pressure level of the sound stimulation received from the paired stimulation control section 75, the amount-of-change extraction section 55 takes an arithmetic mean of the event-related potential cut out at step S104 with respect to each of the right and left ears, each frequency, and each sound pressure level.

At step S106, the amount-of-change extraction section 55 determines whether the number of summations in the arithmetic mean calculation for the event-related potentials in response to the sound stimulation(s) presented at step S102 and step S103 has reached a predetermined number of times. If the number of summations is equal to or less than the predetermined number of times, the process returns to step S101 to repeat presentation of paired stimulations. If the number of summations is equal to or greater than the predetermined number of times, the process proceeds to step S107. The predetermined number of times may be 20 times, for example. Note that "20 times" is a mere example, although it is a number of summations which is frequently adopted in fields where event-related potentials are to be measured. For example, in the amount-of-change extraction section 55, an S(signal)/N(noise) may be determined by assuming that the P1-N1 amplitude is the signal, and a number of summations such that the S/N is equal to or greater than a certain value may be defined as the predetermined number of times.

At step S107, from the event-related potentials to the first sound and second sound with respect to each of the right and left ears, each frequency, and each sound pressure level, which have been subjected to an arithmetic mean calculation over a predetermined number of times, the amount-of-change extraction section 55 calculates a characteristic feature concerning the N1 component and an amount of change thereof. For example, a P1-N1 amplitude may be calculated as the characteristic feature, and a ratio between the P1-N1 amplitudes in response to the first sound and second sound may be calculated as the amount of change. The P1-N1 amplitude may be a value obtained by subtracting the minimum value at a latency of about 100 ms from the maximum value at a latency of about 50 ms, for example. Alternatively, it may be a value obtained by subtracting a zone average potential within ±10 ms of a negative peak at a latency of about 100 ms from a zone average potential within ±10 ms of a positive peak at a latency of about 50 ms, for example. A P1-N1 amplitude ratio is obtained by dividing the P1-N1 amplitude in response to the second sound by the P1-N1 amplitude in response to the first sound, for example. Then, the calculated amount of change in the characteristic feature is sent to the annoyance determination section 100.

At step S108, the annoyance determination section 100 receives the amount of change in the characteristic feature from the amount-of-change extraction section 55, and subjects the amount of change to distinction. The distinction may be based on a comparison between the received amount of change and a predetermined threshold value, for example. The predetermined threshold value may be retained in the annoyance determination section 65, for example. In the case where a P1-N1 amplitude ratio between the first sound and second sound is received as the amount of change, comparison may be conducted by using 0.5 as the predetermined threshold value, for example.

At step S109, the annoyance determination section 100 makes a determination as to annoyance based on the result of distinction at step S108. For example, in the case where a comparison between the P1-N1 amplitude ratio and a predetermined threshold value is performed at step S108, an "annoying" determination is made if the P1-N1 amplitude ratio is smaller than the predetermined threshold value, and an "appropriate loudness" determination is made if it is equal to or greater than the predetermined threshold value.

At step S110, with respect to each of the right and left ears and each frequency of the sound stimulation(s) presented at step S102 and step S103, the result accumulating DB 80 accumulates the information received from the annoyance determination section 65 concerning the annoyance determination result.

At step S111, the presentation sound determination section 70 determines whether presentation has been completed for all of the sound stimulations to be subjected to annoyance assessment. If it is not completed, the process returns to step S101; if it is completed, the annoyance assessment is ended.

With the annoyance assessment system 100 of the present embodiment, when the same sound stimulation is successively presented twice with a predetermined interval therebetween, a UCL is determined based on an amount of change in a characteristic feature concerning the N1 component in response to the first sound and the second sound. As a result, hearing aid fitting can be realized in such a manner that the user will not feel annoyance when the hearing aid is worn.

Note that, as described above, saturation of the amplitude of the N1 component in response to the first sound or the second sound may be utilized as an index of UCL evaluation. Therefore, in the amount-of-change extraction section 55, N1 component amplitudes (P1-N1 amplitude or N1-P2 amplitude) in response to the first sound and second sound and an amount of change in the P1-N1 amplitude between the first sound and second sound may both be extracted. Then, upon detecting saturation of the amplitude of the N1 component in response to the first sound or the second sound and also the P1-N1 amplitude ratio being smaller than a predetermined threshold value, the annoyance determination section 65 may make an annoying determination for that sound stimulation.

Employing both in combination may provide for an improved accuracy of the annoyance assessment.

In the description of the present embodiment, the biological signal measurement section 50 cuts out an event-related potential in a predetermined range based on a trigger from the paired stimulation control section 75 as a starting point, subjects it to baseline correction, and sends the potential waveform data to the amount-of-change extraction section 55. However, this process is an example. In another process, for example, the biological signal measurement section 50 may constantly measure an electroencephalogram, and the amount-of-change extraction section 55 may perform cutting out of an event-related potential and a baseline correction as needed. With such a construction, the paired stimulation control section 75 does not need to send a trigger to the biological signal measurement section 50, but may only send a trigger to the amount-of-change extraction section 55.

Although the present embodiment illustrates that the annoyance assessment results are accumulated in the result accumulating DB 80, accumulation is not necessary. For example, in the case where the result accumulating DB 80 is provided external to the annoyance assessment apparatus 1, each determination result of the annoyance determination section 65 may simply be output. Each determination result can be utilized as information concerning annoyance.

Embodiment 2

In the annoyance assessment system 100 of Embodiment 1, annoyance determination based on an amount of change in a characteristic feature concerning the N1 component between a first sound and a second sound is performed in an exhaustive manner, with respect to every sound stimulation, e.g., from 80 dBSPL to 110 dBSPL, that is stored in the sound DB 71.

However, an exhaustive annoyance assessment which is performed across a wide breadth of sound pressure levels has a problem of time consumingness as well as possibility of hurting the user's ear through presentation of sound stimulations at sound pressure levels which are equal to or greater than the UCL.

Therefore, the present embodiment illustrates an annoyance assessment system which accepts an input of an HTL (i.e., hearing threshold value) of each user, predicts a virtual UCL from the input hearing threshold value, and performs an annoyance assessment that is confined to the neighborhood of the predicted UCL.

Figure 13:
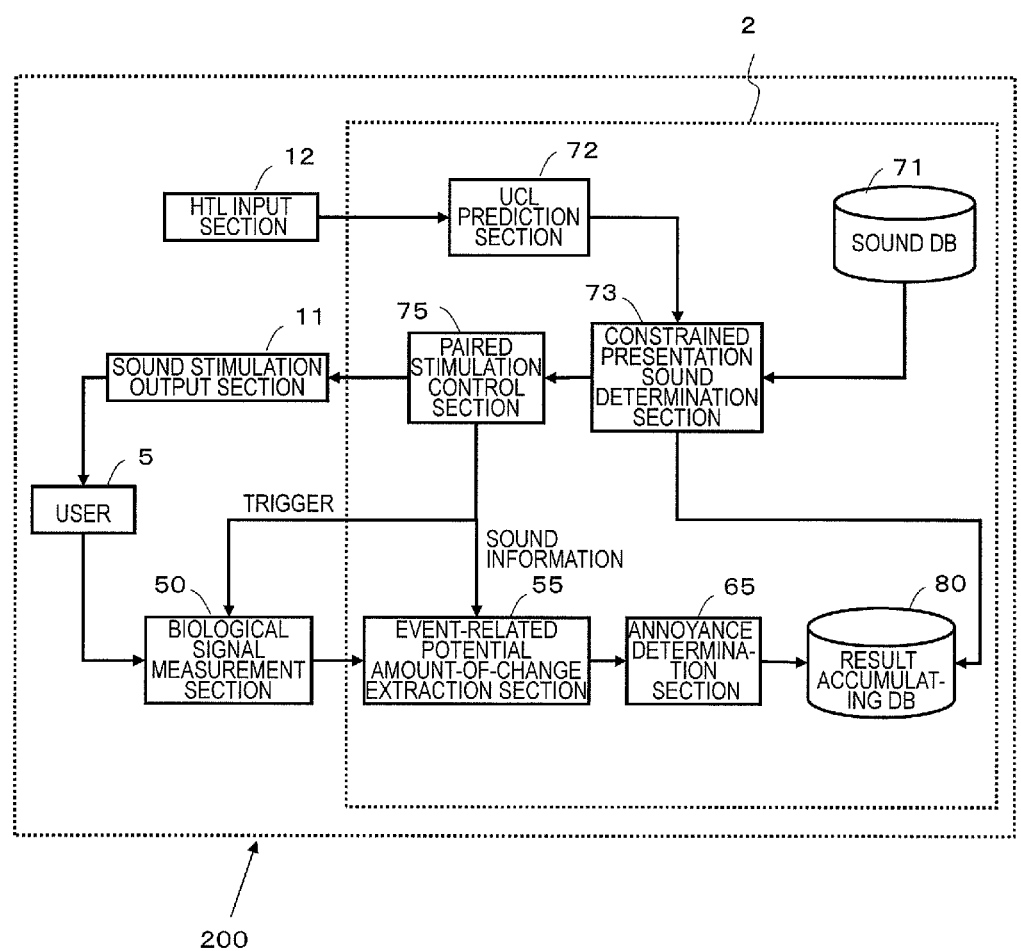
FIG. 13 is a diagram showing a functional block construction of an annoyance assessment system 200 according to Embodiment 2 of the present disclosure.

FIG. 13 shows the functional block construction of an annoyance assessment system 200 according to the present embodiment. The annoyance assessment system 200 includes an HTL input section 12, a sound stimulation output section 11, a biological signal measurement section 50, and an annoyance assessment apparatus 2. The annoyance assessment apparatus 2 is connected to the sound stimulation output section 11, the HTL input section 12, and the biological signal measurement section 50 in a wired or wireless manner. Any block which has an identical counterpart in FIG. 9 is denoted by a like reference numeral, and the description thereof is omitted.

The hardware construction of the annoyance assessment apparatus 2 is as shown in FIG. 8. The annoyance assessment apparatus 2 of the present embodiment shown in FIG. 13 is realized as a program which defines a different process from that of the program 35 described in Embodiment 1 (FIG. 8).

One large difference of the annoyance assessment apparatus 2 of the present embodiment from the annoyance assessment apparatus 1 of Embodiment 1 is that an uncomfortable level (UCL) prediction section 72 is additionally introduced.

Although each component element of the annoyance assessment apparatus 2 is basically given the same name as that used in Embodiment 1, they may be denoted by different reference numerals when having different operations and/or functions. For example, the present embodiment selects sound stimulations confined to sound pressure levels near the predicted UCL, which is not conducted in Embodiment 1; therefore, a constrained presentation sound determination section 73 is provided instead of the presentation sound determination section 70.

Hereinafter, the HTL input section 12, the UCL prediction section 72, and the constrained presentation sound determination section 73 will be described.

From an expert of hearing aid fitting utilizing software for hearing aid fitting, the HTL input section 12 receives separately-acquired information of a hearing threshold value of the user. Then, the HTL input section 12 sends this information to the UCL prediction section 72. This information is threshold value information for each frequency, which is utilized for determining a range in which a test for the user is to be conducted.

Upon receiving the HTL information of each user from the HTL input section 12, the UCL prediction section 72 predicts a UCL for each of the right and left ears and for each frequency. The UCL prediction may be calculated by a method of, as indicated by eq. 1, dividing the HTL value for each of the right and left ears and each frequency by a predetermined value "2", based on the half-gain method, and adding a predetermined value a thereto, for example. For example, predictions are made as indicated in FIG. 14 when the a value is 75. Note that a may be changed from frequency to frequency.

$$\text{UCL value}=\text{HTL}/2+\alpha \qquad (\text{eq. 1})$$

Similarly to the presentation sound determination section 70 of Embodiment 1, the constrained presentation sound determination section 73 refers to the sound DB 71 to determine the right or left ear, frequency, and sound pressure level of the sound stimulation. One difference from the presentation sound determination section 70 is that, based on the UCL prediction value received from the UCL prediction section 72, a sound stimulation is selected from among sound pressure levels within the predetermined range. The predetermined range may be ±5 dB of the UCL prediction value, or ±10 dB, for example, with respect to each of the right and left ears and each frequency. Sound stimulations having sound pressure levels within the predetermined range may be randomly determined under the following constraints, for example: any sound stimulation that is of the same frequency as the immediately previous paired stimulations is preferably not selected; the ear to which the paired stimulations are presented is randomly chosen between the right or left ear; however, it is preferable that not more than four pairs of stimulations are presented successively to either the right or left ear.

Next, with reference to the flowchart of FIG. 15, an overall procedure of processing performed in the annoyance assessment system 200 will be described.

Figure 15:
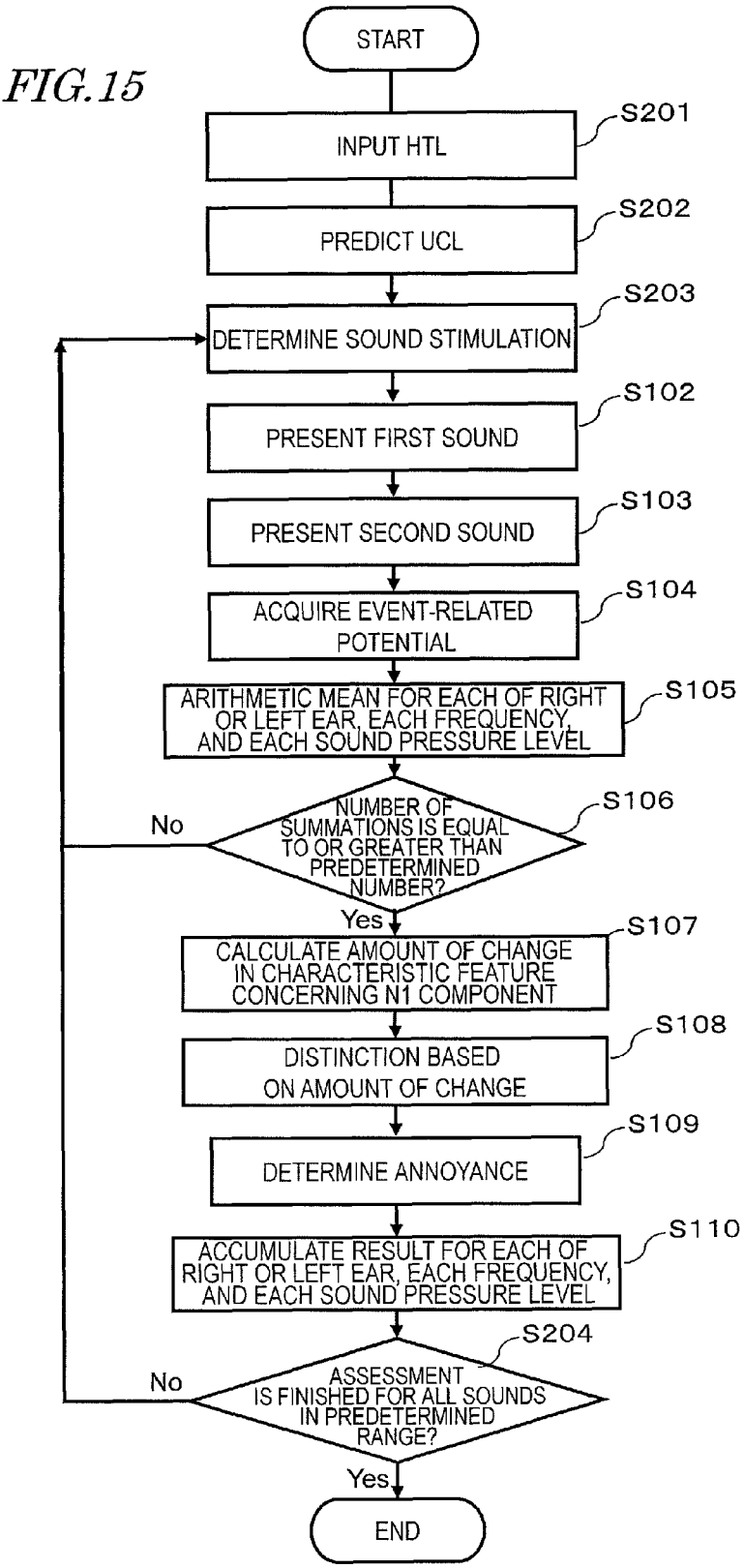
FIG. 15 is a flowchart showing a processing procedure of the annoyance assessment system 200 according to Embodiment 2 of the present disclosure.

FIG. 15 shows a processing procedure by the annoyance assessment system 200 of the present embodiment. In FIG. 15, any step at which the same process as the process by the annoyance assessment system 100 (FIG. 12) is performed is denoted by a like reference numeral, and the description thereof is omitted.

The processes by the annoyance assessment system 200 of the present embodiment differ from the processes by the annoyance assessment system 100 of Embodiment 1 in steps S201, S202, S203, and S204. Any other steps have already been described in connection with FIG. 12, and the descriptions thereof are omitted.

At step S201, from an expert conducting the hearing aid fitting, the HTL input section 12 receives separately-acquired information of a hearing threshold value of the user for each of the right and left ears and each frequency. Then, this information is sent to the UCL prediction section 72.

At step S202, upon receiving the HTL information of each user from the HTL input section 12, the UCL prediction section 72 predicts a UCL for each of the right and left ears and each frequency. The UCL prediction may be calculated by a method of, as indicated by eq. 1, dividing the HTL value for each of the right and left ears and each frequency by a predetermined value "2" and adding a predetermined value a thereto, for example.

At step S203, the constrained presentation sound determination section 73 selects and determines a sound stimulation from among the sound pressure levels within a predetermined range around the virtual UCL sound pressure level as predicted by the UCL prediction section 72. The predetermined range may be ±5 dB of the UCL prediction value, or ±10 dB, for example, with respect to each of the right and left ears and each frequency. Sound stimulations may be randomly determined under the following constraints from within the predetermined range, for example: any sound stimulation that is of the same frequency as the immediately previous paired stimulations is preferably not selected; the ear to which the paired stimulations are presented is randomly chosen between the right or left ear; however, it is preferable that not more than four pairs of stimulations are presented successively to either the right or left ear.

Then, at step S204, the constrained presentation sound determination section 73 determines whether assessment has been finished for every sound in the predetermined range.

Through such processes, a UCL, i.e., a sound pressure level so loud that it is felt uncomfortable to the user, can be measured in a short time and with a high accuracy, for example.

In accordance with the annoyance assessment system 200 of the present embodiment, it is possible to perform an annoyance assessment for sound pressure levels within a predetermined range based on a virtual UCL sound pressure level which is predicted from an input HTL. As a result, evaluation of the UCL of the user can be realized in a shorter time.

Note that the annoyance assessment system 100 shown in FIG. 9 and the annoyance assessment system 200 shown in FIG. 13 may each be constructed as an integral apparatus.

Figure 16:
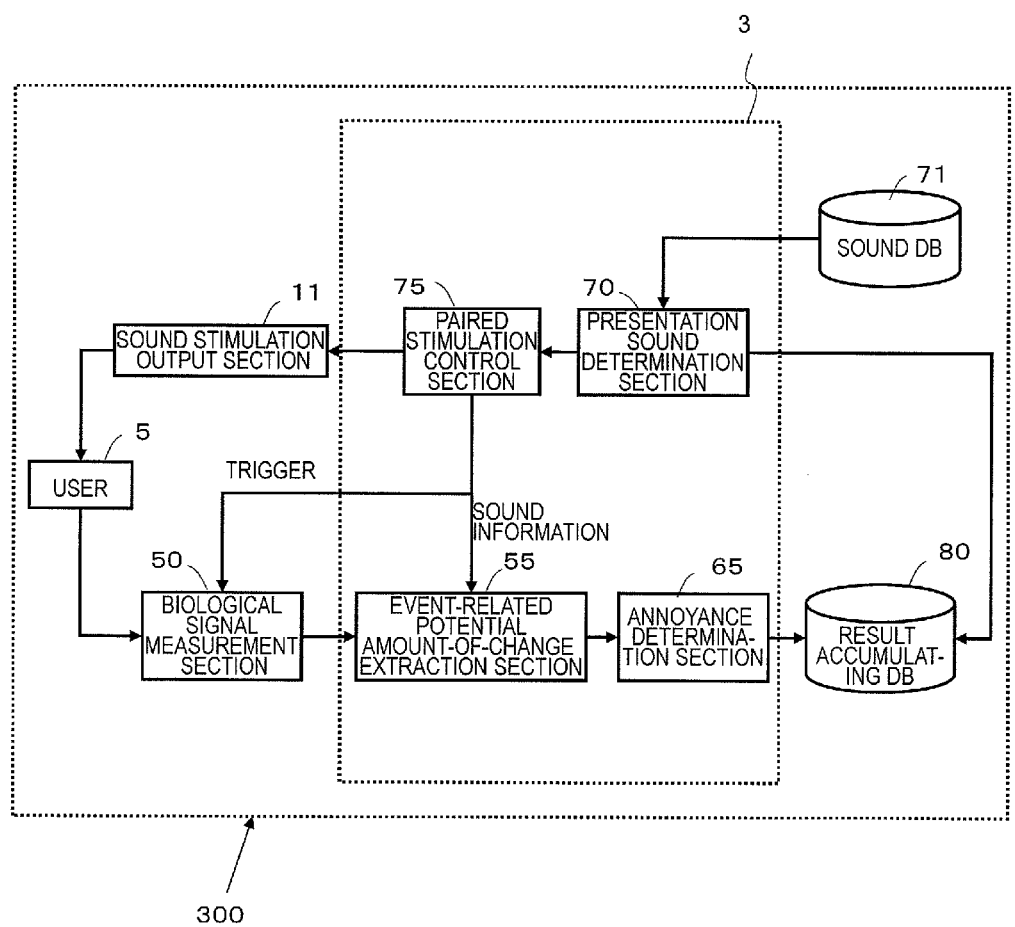
FIG. 16 is a diagram showing a functional block construction of an annoyance assessment system 300 according to Embodiment 2 of the present disclosure.

Alternatively, an annoyance assessment apparatus 3 shown in FIG. 16 includes an amount-of-change extraction section 55, an annoyance determination section 65, a presentation sound determination section 70, and a paired stimulation control section 75. An annoyance assessment system 300 includes a sound stimulation output section 11, a biological signal measurement section 50, a sound DB 71, a result accumulating DB 80, and the annoyance assessment apparatus 3.

The annoyance assessment apparatus 3 is identical to the annoyance assessment apparatus 1 shown in FIG. 9 except that the sound DB 71 and the result accumulating DB 80 are omitted. The annoyance assessment apparatus 3 is connected to the sound DB 71 and the result accumulating DB 80 in a wired or wireless manner, thus performing sending and receiving of information.

Figure 17:
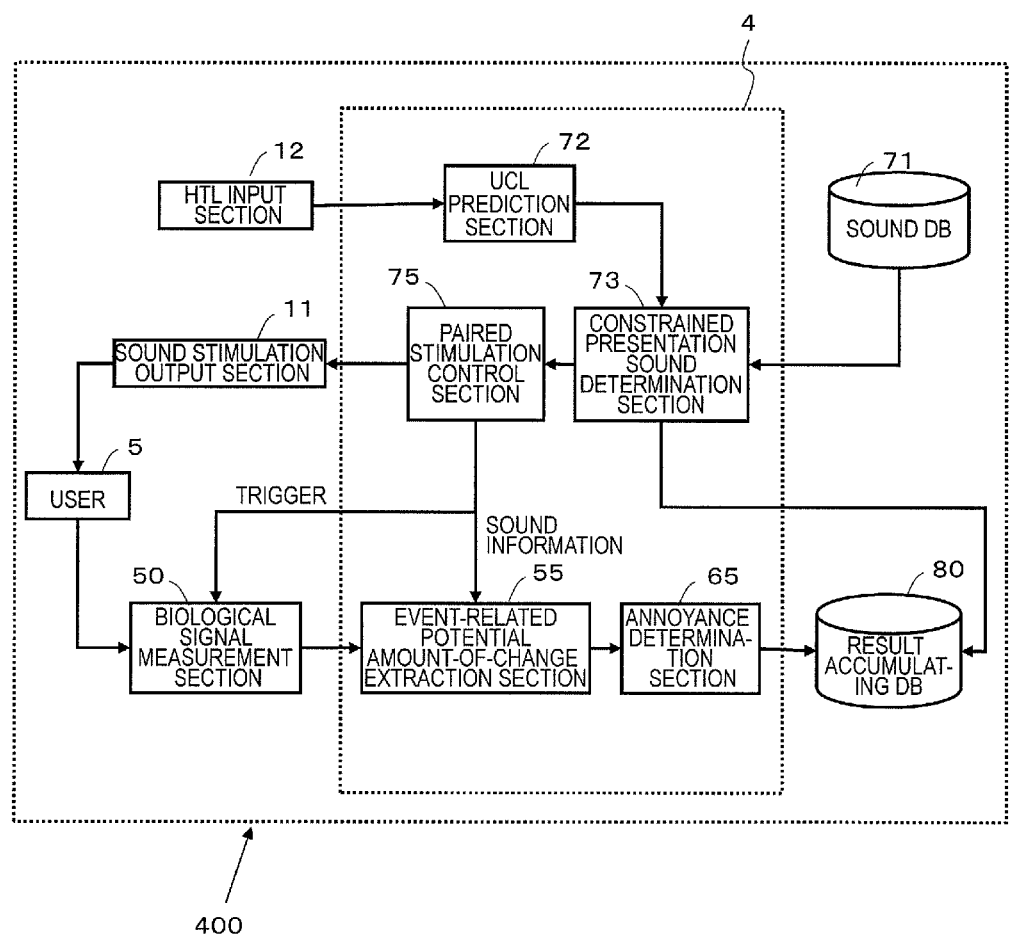
FIG. 17 is a diagram showing a functional block construction of an annoyance assessment system 400 according to Embodiment 2 of the present disclosure.

Alternatively, an annoyance assessment apparatus 4 shown in FIG. 17 includes an amount-of-change extraction section 55, an annoyance determination section 65, a UCL prediction section 72, a constrained presentation sound determination section 73, and a paired stimulation control section 75. An annoyance assessment system 400 includes an HTL input section 12, a sound stimulation output section 11, a biological signal measurement section 50, a sound DB 71, a result accumulating DB 80, and the annoyance assessment apparatus 4.

The annoyance assessment apparatus 4 is identical to the annoyance assessment apparatus 2 shown in FIG. 16 except that the sound DB 71 and the result accumulating DB 80 are omitted. The annoyance assessment apparatus 4 is connected to the sound DB 71 and the result accumulating DB 80 in a wired or wireless manner, thus performing sending and receiving of information.

Embodiments of the present disclosure have been described above.

Note that, in the present specification, "annoyance assessment apparatus system", "annoyance assessment apparatus", and "annoyance assessment method" are also referred to as "sound pressure assessment system", "sound pressure assessment apparatus", and "sound pressure assessment method", respectively.

With a sound pressure assessment apparatus and an annoyance assessment system incorporating the sound pressure assessment apparatus according to any embodiment of the present disclosure, it is possible to assess whether a sound pressure level is so annoying that it is felt uncomfortable to a user, objectively and with a high accuracy. As a result, a hearing aid fitting is realized without allowing the user to feel annoyed and without inducing aural fatigue. Thus, the technique disclosed herein is available to the fitting of any and all hearing aid users.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. A sound pressure assessment system comprising:
   one or more memories storing a sound database retaining data of a plurality of sounds, each sound being a pure tone; and
   circuitry which in operation is configured to:
   measure an electroencephalogram signal of a user;
   determine a plurality of sounds to be presented by referring to the sound database;
   present the determined plurality of sounds as a first sound to the user, and in a predetermined time after presenting the first sound, present as a second sound a sound at least having a same frequency and a same sound pressure level as those of the first sound to the user;
   extract an amount of change from an N1 component in response to the first sound to an N1 component in response to the second sound, the N1 component in response to the first sound being a negative component of an event-related potential of the electroencephalogram signal based on a point of presenting the first sound as a starting point, the N1 component in response to the second sound being a negative component of an event-related potential of the electroencephalogram signal based on a point of presenting the second sound as a starting point; and
   determine whether the sound pressure level of the presented sounds is excessive to the user, based on the amount of change extracted.

2. The sound pressure assessment system of claim 1, wherein,
   as the amount of change, the circuitry is configured to determine an amplitude ratio obtained by dividing an amplitude derived from the N1 component in response to the second sound by an amplitude derived from the N1 component in response to the first sound; and
   the circuitry is configured to compare the amount of change against a predetermined threshold value, and if the amount of change is smaller than the predetermined threshold value, to determine that the sound pressure level of the presented sound is annoying to the user, and if the amount of change is equal to or greater than the predetermined threshold value, to determine that the sound pressure level of the presented sound is an appropriate sound pressure level for the user.

3. The sound pressure assessment system of claim 1, wherein,
   the circuitry is configured to present a plurality of pairs of stimulations, each pair including a said first sound and a said second sound; and
   for each pair of stimulations, the circuitry is configured to extract an amount of change from an amplitude of a P1 component in response to the first sound, the P1 component being a positive component of an event-related potential of the electroencephalogram signal based on the point of presenting the first sound as a starting point, to an amplitude of a P1 component in response to the second sound, the P1 component being a positive component of an event-related potential of the electroencephalogram signal based on the point of presenting the second sound as a starting point, to take an arithmetic mean of event-related potentials of the extracted electroencephalogram signal for each of the first sounds and the second sounds of the plurality of pairs, and to extract as the amount of change a ratio of: a difference between an arithmetic-meaned amplitude value of the P1 component in response to the first sound and an arithmetic-meaned amplitude value of the N1 component in response to the first sound; and a difference between an arithmetic-meaned amplitude value of the P1 component in response to the second sound and an arithmetic-meaned amplitude value of the N1 component in response to the second sound.

4. The sound pressure assessment system of claim 1, wherein,
   as the amount of change, the circuitry is configured to determine an absolute value of the difference between an amplitude derived from the N1 component in response to the second sound and an amplitude derived from the N1 component in response to the first sound; and
   the circuitry is configured to compared the amount of change against a predetermined threshold value, and if the amount of change is equal to or greater than the predetermined threshold value, to determine that the sound pressure level of the presented sound is annoying to the user, and if the amount of change is smaller than the predetermined threshold value, to determine that the sound pressure level of the presented sound is an appropriate sound pressure level for the user.

5. The sound pressure assessment system of claim 1, wherein the N1 component is a negative component of an event-related potential in a range from 80 ms to 130 ms after a point of presenting the first sound or the second sound.

6. The sound pressure assessment system of claim 3, wherein the P1 component is a positive component of an event-related potential in a range from 30 ms to 70 ms after a point of presenting the first sound or the second sound.

7. The sound pressure assessment system of claim 1, wherein,
the sound database retains each sound in association with at least one sound characteristic feature, the at least one sound characteristic feature including a right or left ear of the user to which the sound is presented, a frequency of the sound, and/or a sound pressure level of the sound; and
the circuitry is configured to take an arithmetic mean of event-related potentials of the electroencephalogram signal for each of the first sound and the second sound and each sound characteristic feature.

8. The sound pressure assessment system of claim 3, wherein,
the circuitry is configured to calculate a P1-N1 amplitude concerning an event-related potential in response to the first sound and the second sound, the P1-N1 amplitude being a difference between a positive peak value respectively of an event-related potential from 30 ms to 70 ms after the point of presenting the first sound and the second sound as a starting point and a negative peak value from 80 ms to 150 ms after the point of presenting the first sound and the second sound as a starting point, and to extract as the amount of change an amplitude ratio between the P1-N1 amplitude in response to the second sound and the P1-N1 amplitude in response to the first sound; and
if the amplitude ratio is smaller than a first threshold value, the circuitry is configured to determine that the sound pressure level of the presented sound is annoying to the user, and if the amplitude ratio is equal to or greater than the first threshold value, the circuitry is configured to determine that the sound pressure level of the presented sound is an appropriate sound pressure level for the user.

9. The sound pressure assessment system of claim 8, wherein the first threshold value is 0.5.

10. The sound pressure assessment system of claim 1, wherein,
the circuitry is configured to present a plurality of pairs of stimulations, each pair including a said first sound and a said second sound; and
for each pair of stimulations, the circuitry is configured to extract a P2 component in response to the first sound, the P2 component being a positive component of the electroencephalogram signal from 160 ms to 250 ms after the point of presenting the first sound as a starting point, and a P2 component in response to the second sound, the P2 component being a positive component of the electroencephalogram signal from 160 ms to 250 ms after the point of presenting the second sound as a starting point, to take an arithmetic mean of event-related potentials of the P2 components for each of the first sounds and the second sounds of the plurality of pairs, and to extract as the amount of change a ratio of: a difference between an arithmetic-meaned amplitude value of the P2 component in response to the first sound and an arithmetic-meaned amplitude value of the N1 component in response to the first sound; to a difference between an arithmetic-meaned amplitude value of the P2 component in response to the second sound and an arithmetic-meaned amplitude value of the N1 component in response to the second sound.

11. The sound pressure assessment system of claim 10, wherein,
the circuitry is configured to calculate an N1-P2 amplitude concerning an event-related potential in response to the first sound and the second sound, the N1-P2 amplitude being a difference respectively between a negative peak value from 80 ms to 150 ms after the point of presenting the first sound and the second sound as a starting point and a positive peak value of an event-related potential from 160 ms to 250 ms after the point of presenting the first sound and the second sound as a starting point, and to extract as the amount of change an amplitude ratio between the N1-P2 amplitude in response to the second sound and the N1-P2 amplitude in response to the first sound; and
if the amplitude ratio is smaller than a second threshold value, the circuitry is configured to determine that the sound pressure level of the presented sound is annoying to the user, and if the amplitude ratio is equal to or greater than the second threshold value, the circuitry is configured to determine that the sound pressure level of the presented sound is an appropriate sound pressure level for the user.

12. The sound pressure assessment system of claim 11, wherein the second threshold value is 0.55.

13. The sound pressure assessment system of claim 1, wherein the circuitry is configured to present a plurality of pairs of stimulations, each pair including a said first sound and a said second sound, and presents a pair of stimulations of a different frequency from that of any immediately previously-presented pair of stimulations.

14. The sound pressure assessment system of claim 1, wherein the circuitry further is configured to:
receive a hearing threshold value of the user; and
predict an uncomfortable level of the user based on the hearing threshold value, wherein
the circuitry is configured to determine the first sound and the second sound from within a predetermined range around the predicted uncomfortable level.

15. A sound pressure assessment apparatus comprising circuitry which in operation is configured to:
measure an electroencephalogram signal of a user;
determine a plurality of sounds to be presented by referring to a sound database retaining data of a plurality of sounds, each sound being a pure tone;
present the determined plurality of sounds as a first sound to the user, and in a predetermined time after presenting the first sound, present as a second sound a sound at least having a same frequency and a same sound pressure level as those of the first sound to the user;
extract an amount of change from an N1 component in response to the first sound to an N1 component in response to the second sound, the N1 component in response to the first sound being a negative component of an event-related potential of the electroencephalogram signal based on a point of presenting the first sound as a starting point, the N1 component in response to the second sound being a negative component of an event-related potential of the electroencephalogram signal based on a point of presenting the second sound as a starting point; and
determine annoyance with respect to the sound pressure level of the presented sounds, based on the amount of change extracted.

16. A sound pressure assessment system comprising:
one or more memories storing a sound database retaining data of a plurality of sounds, each sound being a pure tone; and
circuitry which in operation is configured to:
measure an electroencephalogram signal of a user;
determine a plurality of sounds to be presented by referring to the sound database;
present the determined plurality of sounds as a first sound to the user, and in a predetermined time after presenting the first sound, present as a second sound a sound at least having a same frequency and a same sound pressure level as those of the first sound to the user;
extract an amount of change from an event-related potential in a zone from −100 milliseconds to 400 milliseconds based on a point of presenting the first sound as a starting point, to an event-related potential in a zone from −100 milliseconds to 400 milliseconds based on a point of presenting the second sound as a starting point; and
determine whether the sounds pressure level of the presented sound is excessive to the user, based on the amount of change.

17. A sound pressure assessment method comprising the steps of:
measuring an electroencephalogram signal of a user;
determining a plurality of sounds to be presented to the user;
presenting the determined plurality of sounds as a first sound to the user, and in a predetermined time after presenting the first sound, presenting as a second sound the same sound as the first sound to the user;
extracting an amount of change from an N1 component in response to the first sound to an N1 component in response to the second sound, the N1 component in response to the first sound being a negative component of an event-related potential of the electroencephalogram signal based on a point of presenting the first sound as a starting point, the N1 component in response to the second sound being a negative component of an event-related potential of the electroencephalogram signal based on a point of presenting the second sound as a starting point; and
determining annoyance with respect to the sound pressure levels of the presented sounds, based on the extracted amount of change.

18. The sound pressure assessment method of claim 17, wherein the step of determining annoyance compares the amount of change against a predetermined threshold value, and if the amount of change is smaller than the predetermined threshold value, determines that the sound pressure level of the presented sound is annoying to the user, and if the amount of change is equal to or greater than the predetermined threshold value, determines that the sound pressure level of the presented sound is an appropriate sound pressure level for the user.

19. A non-transitory computer-readable medium storing a computer program, to be executed by a computer,
wherein the computer program causes the computer to execute the steps of:
receiving an electroencephalogram signal of a user;
determining a plurality of sounds to be presented to the user;
presenting the determined plurality of sounds as a first sound to the user, and in a predetermined time after presenting the first sound, presenting as a second sound the same sound as the first sound to the user;
extracting an amount of change from an N1 component in response to the first sound to an N1 component in response to the second sound, the N1 component in response to the first sound being a negative component of an event-related potential of the electroencephalogram signal based on a point of presenting the first sound as a starting point, the N1 component in response to the second sound being a negative component of an event-related potential of the electroencephalogram signal based on a point of presenting the second sound as a starting point; and
determining annoyance with respect to the sound pressure levels of the presented sounds, based on the extracted amount of change.

20. The non-transitory computer-readable medium of claim 19, wherein the step of determining annoyance compares the amount of change against a predetermined threshold value, and if the amount of change is smaller than the predetermined threshold value, determines that the sound pressure level of the presented sound is annoying to the user, and if the amount of change is equal to or greater than the predetermined threshold value, determines that the sound pressure level of the presented sound is an appropriate sound pressure level for the user.

* * * * *